(12) United States Patent
Brophy et al.

(10) Patent No.: US 7,294,734 B2
(45) Date of Patent: *Nov. 13, 2007

(54) PROCESS FOR CONVERTING A HYDROCARBON TO AN OXYGENATE OR A NITRILE

(75) Inventors: John H. Brophy, Bristol (GB); Frederick A. Pesa, Aurora, OH (US); Anna Lee Tonkovich, Marysville, OH (US); Jeffrey S. McDaniel, Columbus, OH (US); Kai Tod Paul Jarosch, Bexley, OH (US)

(73) Assignee: Velocys, Inc., Plain City, OH (US)

( * ) Notice: Subject to any disclaimer, the term of this patent is extended or adjusted under 35 U.S.C. 154(b) by 280 days.

This patent is subject to a terminal disclaimer.

(21) Appl. No.: 10/429,286

(22) Filed: May 2, 2003

(65) Prior Publication Data

US 2004/0220434 A1 Nov. 4, 2004

(51) Int. Cl.
  *C07C 253/24* (2006.01)
  *C07C 51/215* (2006.01)
  *C07C 27/14* (2006.01)
(52) U.S. Cl. ............... 558/317; 558/318; 562/418; 562/532; 562/542; 568/959
(58) Field of Classification Search ......... 562/418, 562/532, 542; 558/317, 318; 568/959
  See application file for complete search history.

(56) References Cited

U.S. PATENT DOCUMENTS

| | | | |
|---|---|---|---|
| 4,082,785 A | 4/1978 | Fattore et al. ............ 260/465.3 |
| 4,392,362 A | 7/1983 | Little ........................... 62/514 |
| 4,516,632 A | 5/1985 | Swift et al. ................ 165/167 |
| 4,524,236 A | 6/1985 | McCain ...................... 585/658 |
| 5,093,299 A | 3/1992 | Suresh et al. .............. 502/212 |
| 5,162,578 A | 11/1992 | McCain, Jr. et al. ...... 562/512.2 |
| 5,198,580 A | 3/1993 | Bartek et al. .............. 562/542 |
| 5,258,543 A | 11/1993 | Suresh et al. .............. 558/325 |
| 5,309,637 A | 5/1994 | Moriarty ................ 29/890.054 |
| 5,317,805 A | 6/1994 | Hoopman et al. ........ 29/890.03 |
| 5,593,935 A * | 1/1997 | Golunski et al. ........... 502/339 |
| 5,611,214 A | 3/1997 | Wegeng et al. .............. 62/498 |
| 5,618,974 A | 4/1997 | Kurimoto et al. .......... 562/532 |
| 5,686,373 A * | 11/1997 | Tenten et al. .............. 502/312 |
| 5,727,618 A | 3/1998 | Mundinger et al. ........ 165/80.4 |
| 5,811,062 A | 9/1998 | Wegeng et al. ............ 422/129 |
| 5,858,314 A | 1/1999 | Hsu et al. ................... 422/211 |
| 5,997,826 A | 12/1999 | Lodeng et al. ............. 422/190 |
| 6,126,723 A | 10/2000 | Drost et al. ...................... 96/4 |
| 6,129,973 A | 10/2000 | Martin et al. .............. 428/166 |
| 6,130,183 A | 10/2000 | Herskowitz et al. ....... 502/349 |
| 6,143,921 A | 11/2000 | Karim et al. ............... 560/245 |
| 6,162,760 A | 12/2000 | Brazdil, Jr. ................. 502/353 |
| 6,192,596 B1 | 2/2001 | Bennett et al. ................. 34/76 |
| 6,200,536 B1 | 3/2001 | Tonkovich et al. ......... 422/177 |
| 6,216,343 B1 | 4/2001 | Leland et al. .......... 29/890.032 |
| 6,220,497 B1 | 4/2001 | Benz et al. ................. 228/118 |
| 6,230,408 B1 | 5/2001 | Ehrfeld et al. ......... 29/890.039 |
| 6,235,678 B1 | 5/2001 | Mamedov et al. .......... 502/354 |
| 6,239,325 B1 | 5/2001 | Kishimoto et al. ......... 585/658 |
| 6,251,821 B1 | 6/2001 | Hecquet et al. ............. 502/306 |
| 6,252,122 B1 | 6/2001 | Tenten et al. ............... 568/475 |
| 6,268,529 B1 | 7/2001 | Suresh et al. ............... 562/546 |
| 6,274,764 B1 | 8/2001 | Karim et al. ............... 562/548 |
| 6,281,378 B1 | 8/2001 | Kishimoto et al. ......... 558/303 |
| 6,310,240 B1 | 10/2001 | Contractor et al. ......... 562/535 |
| 6,310,241 B1 | 10/2001 | Karim et al. ............... 562/549 |
| 6,313,063 B1 | 11/2001 | Rytter et al. ................ 502/327 |
| 6,313,393 B1 | 11/2001 | Drost ......................... 136/201 |
| 6,333,444 B1 | 12/2001 | Ellis et al. .................. 585/658 |
| 6,352,577 B1 | 3/2002 | Martin et al. .................... 96/4 |
| 6,355,854 B1 | 3/2002 | Liu ............................. 585/658 |
| 6,381,846 B2 | 5/2002 | Insley et al. ........... 29/890.039 |
| 6,383,973 B1 | 5/2002 | Kimura et al. ............. 502/300 |
| 6,383,977 B1 | 5/2002 | Karim et al. ............... 502/311 |
| 6,384,275 B2 | 5/2002 | Lee et al. ................... 562/535 |
| 6,388,129 B1 | 5/2002 | Machhammer et al. .... 562/545 |
| 6,395,936 B1 | 5/2002 | Arnold et al. .............. 568/476 |

(Continued)

FOREIGN PATENT DOCUMENTS

CA 2247662 3/1999

(Continued)

OTHER PUBLICATIONS

The Merck Index, Twelfth Edition.*

(Continued)

*Primary Examiner*—Johann Richter
*Assistant Examiner*—Ebenezer Sackey
(74) *Attorney, Agent, or Firm*—Renner, Otto, Boisselle & Sklar, LLP

(57) ABSTRACT

This invention relates to a process for converting a hydrocarbon reactant to a product comprising an oxygenate or a nitrile, the process comprising: (A) flowing a reactant composition comprising the hydrocarbon reactant, and oxygen or a source of oxygen, and optionally ammonia, through a microchannel reactor in contact with a catalyst to convert the hydrocarbon reactant to the product, the hydrocarbon reactant undergoing an exothermic reaction in the microchannel reactor; (B) transferring heat from the microchannel reactor to a heat exchanger during step (A); and (C) quenching the product from step (A).

91 Claims, 4 Drawing Sheets

U.S. PATENT DOCUMENTS

| | | | |
|---|---|---|---|
| 6,403,829 B1 | 6/2002 | Unverricht et al. | 562/532 |
| 6,410,785 B1 | 6/2002 | Zehner et al. | 562/532 |
| 6,410,800 B1 | 6/2002 | Chang et al. | 568/479 |
| 6,413,903 B1 | 7/2002 | Kourtakis | 502/209 |
| 6,415,860 B1 | 7/2002 | Kelly et al. | 165/748 |
| 6,423,875 B1 | 7/2002 | Machhammer et al. | 568/476 |
| 6,426,433 B1 | 7/2002 | Machhammer et al. | 562/545 |
| 6,429,332 B1 | 8/2002 | Tanimoto et al. | 562/532 |
| 6,437,193 B1 | 8/2002 | Contractor et al. | 568/479 |
| 6,441,227 B1 | 8/2002 | Karim et al. | 562/548 |
| 6,486,091 B1 | 11/2002 | Abdulwahed et al. | 502/312 |
| 6,488,838 B1 | 12/2002 | Tonkovich et al. | 208/108 |
| 6,492,299 B1 | 12/2002 | Couves et al. | 502/339 |
| 6,540,975 B2 | 4/2003 | Tonkovich et al. | 423/659 |
| 6,660,681 B1 | 12/2003 | Ledoux et al. | 502/209 |
| 6,675,875 B1 | 1/2004 | Vafai et al. | 165/80.4 |
| 6,746,651 B1 | 6/2004 | Ponzo et al. | 422/220 |
| 6,746,819 B1 | 6/2004 | Schmitz et al. | 430/272.1 |
| 6,747,178 B1 | 6/2004 | Harston et al. | 570/175 |
| 6,749,814 B1 | 6/2004 | Bergh et al. | 422/130 |
| 6,749,817 B1 | 6/2004 | Mulvaney, III | 422/200 |
| 6,755,211 B1 | 6/2004 | O'Connor et al. | 137/554 |
| 6,756,340 B2 | 6/2004 | Voskoboynikov et al. | 502/328 |
| 6,756,515 B2 | 6/2004 | Rende et al. | 585/444 |
| 6,764,660 B1 | 7/2004 | Wiede, Jr. et al. | 422/198 |
| 6,769,444 B2 | 8/2004 | Guzman et al. | 137/15.01 |
| 6,770,245 B2 | 8/2004 | Akporiaye et al. | 422/82.12 |
| 6,773,684 B2 | 8/2004 | Lesieur et al. | 422/198 |
| 6,969,746 B2 | 11/2005 | Krull et al. | 526/64 |
| 2002/0028164 A1 | 3/2002 | Schutte et al. | 422/198 |
| 2002/0049136 A1 | 4/2002 | Kourtakis et al. | 502/300 |
| 2002/0142914 A1 | 10/2002 | Devlin et al. | 502/300 |
| 2003/0045747 A1 | 3/2003 | Wurziger et al. | 562/418 |
| 2003/0236432 A1 | 12/2003 | Kourtakis et al. | 562/542 |
| 2004/0034266 A1* | 2/2004 | Brophy et al. | 585/658 |
| 2004/0104010 A1 | 6/2004 | Kenny et al. | 165/80.4 |
| 2004/0107831 A1 | 6/2004 | Graham et al. | 95/96 |
| 2004/0123626 A1 | 7/2004 | Caze et al. | 65/17.2 |
| 2004/0125689 A1 | 7/2004 | Ehrfeld et al. | 366/165.1 |
| 2004/0127352 A1 | 7/2004 | Jin et al. | 502/322 |
| 2004/0130057 A1 | 7/2004 | Mehrabi et al. | 264/171.13 |
| 2004/0131345 A1 | 7/2004 | Kylberg et al. | 392/465 |
| 2004/0131507 A1 | 7/2004 | Saitmacher et al. | 422/111 |
| 2004/0131829 A1 | 7/2004 | Joseph et al. | 428/166 |
| 2004/0132832 A1 | 7/2004 | Espinoza et al. | 518/716 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |

FOREIGN PATENT DOCUMENTS

| | | |
|---|---|---|
| EP | 0 903 174 A1 | 3/1999 |
| EP | 1 311 341 B1 | 8/2001 |
| EP | 0 904 608 B1 | 12/2001 |
| EP | 1 312 411 A2 | 5/2003 |
| EP | 1 312 411 A3 | 7/2003 |
| EP | 1 382 382 A1 | 7/2003 |
| WO | 95/05895 | 3/1995 |
| WO | 97/32687 | 9/1997 |
| WO | 98/55812 | 12/1998 |
| WO | 00/06295 | 2/2000 |
| WO | 01/10773 A1 | 2/2001 |
| WO | 01/12312 A2 | 2/2001 |
| WO | 01/54807 * | 8/2001 |
| WO | 01/54807 A1 | 8/2001 |
| WO | 01/68636 A1 | 9/2001 |
| WO | 01/83466 A1 | 11/2001 |
| WO | 01/95237 A2 | 12/2001 |
| WO | 03/026788 | 4/2003 |
| WO | 03/078052 A1 | 9/2003 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067492 | 8/2004 |
| WO | 2004/067708 | 8/2004 |

OTHER PUBLICATIONS

Excepts from The Chemistry of the Cyano Group, 1970, Edited by Zvi Rappoport.*

Besser, Ronald S. "New Directions in Reactor Design Through Miniaturization". Sep. 13, 2002, Tulane Engineering Forum.

Ouyang et al. "Flexible Microreactor System for Chemical Research at Moderate and High Temperatures". Stevens Institute of Technology.

Written Opinion and International Search Report, Application No. PCT/US2004/012870, mailed Sep. 14, 2004.

Waku et al.; "Effects of $O_2$ Concentration on the Rate and Selectivity in Oxidative Dehydrogenation of Ethane Catalyzed by Vanadium Oxide: Implications for $O_2$ Staging and Membrane Reactors"; Ind. Eng. Chem. Res. 2003, 41, 5462-5466.

Matlosz et al.; "Microreactors as Tools in Chemical Research"; Microreaction Technology; IMRET 5: Proceedings of the Fifth International Conference on Microreaction Technology. (May 27-30, 2001).

Srinivasn et al.; "Micromachined Reactors for Catalytic Partial Oxidation Reactions"; AIChE Journal; Nov. 1997; vol. 43, No. 11; pp. 3059-3069.

TeGrotenhuis et al.; Optimizing Microchannel Reactors by Trading-Off Equilibrium and Reaction Kinetics through Temperature Management; Prepared for presentation at IMRET 6—6th International Conference on Microreaction Technology; Mar. 10-14, 2002.

Wegeng et al.; "Compact Fuel Processors for Fuel Cell Powered Automobiles Based on Microchannel Technology"; Fuel Cells Bulletin No. 28; pp. 8-13.

Rostami et al.; "Flow and Heat Transfer for Gas Flowing in Microchannels: a Review"; Heat and Mass Transfer 38 (2002) 359-367.

Matlosz et al.; "Selective Oxidation of 1-Butene to Maleic Anhydride—Comparison of the Performance between Microchannel Reactors and a Fixed Bed Reactor"; Microreaction Technology; IMRET 5: Proceedings of the Fifth International Conference on Microreaction Technology. (2001).

Steinfeldt et al.; "Comparative Studies of the Oxidative Dehydrogenation of Propane in Micro-Channels Reactor Module and Fixed-Bed Reactor"; Studies in Surface Science and Catalysis; 2001 Elsevier Science B.V.; pp. 185-190.

Beretta et al.; "Production of Olefins via Oxidative Dehydrogenation of Light Paraffins at Short Contact Times"; Catalysis Today; 2001 Elsevier Science B.V.; pp. 103-111.

International Preliminary Report on Patentability, Application No. PCT/US2004/012870, mailed Sep. 9, 2005.

Johnston et al.; "Application of Printed Circuit Heat Exchanger Technology within Heterogeneous Catalytic Reactors"; presented at the AIChE Annual Meeting 2001.

Tonkovich et al.; "The Catalytic Partial Oxidation of Methane in a Microchannel Chemical Reactor"; Proceedings of the Second International Conference of Microreaction Technology, Mar. 1998.

Matlosz et al.; "Microreactors as Tools in Chemical Research"; Microreaction Technology; IMRET 5: Proceedings of the Fifth International Conference on Microreaction Technology. (May 27-30, 2001).

Srinivasn et al.; "Micromachined Reactors for Catalytic Partial Oxidation Reactions"; AIChE Journal; Nov. 1997; vol. 43, No. 11; pp. 3059-3069.

TeGrotenhuis et al.; Optimizing Microchannel Reactors by Trading-Off Equilibrium and Reaction Kinetics through Temperature Management; Prepared for presentation at IMRET 6—6th International Conference on Microreaction Technology; Mar. 10-14, 2002.

Wegeng et al.; "Compact Fuel Processors for Fuel Cell Powered Automobiles Based on Microchannel Technology"; Fuel Cells Bulletin No. 28; pp. 8-13, no date available.

Rostami et al.; "Flow and Heat Transfer for Gas Flowing in Microchannels: a Review"; Heat and Mass Transfer 38 (2002) 359-367.

Matlosz et al.; "Selective Oxidation of 1-Butene to Maleic Anhydride—Comparison of the Performance between Microchannel Reactors and a Fixed Bed Reactor"; Microreaction Technology; IMRET 5: Proceedings of the Fifth International Conference on Microreaction Technology. (2001).

Steinfeldt et al.; "Comparative Studies of the Oxidative Dehydrogenation of Propane in Micro-Channels Reactor Module and Fixed-Bed Reactor"; Studies in Surface Science and Catalysis; 2001 Elsevier Science B.V.; pp. 185-190.

Gohring et al.; "Gas Phase Reactions in Ceramic Microreactors"; IMERT 6, 10-14, Marz 2002, New Orleans, USA, AlChE Conference Proceedings 55-60.

Hsing et al.; "Simulation of Microchannel Chemical Reactors for Heterogeneous Partial Oxidation Reactions"; Chemical Engineering Science 55 (2000) 3-13.

* cited by examiner

PROCESS FOR CONVERTING A HYDROCARBON TO AN OXYGENATE OR A NITRILE

TECHNICAL FIELD

This invention relates to a process for converting a hydrocarbon reactant to an oxygenate or a nitrile using microchannel process technology.

BACKGROUND OF THE INVENTION

Oxidation reactions typically involve reacting a hydrocarbon with oxygen in the presence of a catalyst to form an oxygenate. Examples include the conversion of methane to methanol or formaldehyde; ethane or ethylene to ethyl alcohol, ethylene oxide, acetic acid or vinyl acetate; or propylene to acrylic acid or acrolein. Ammoxidation reactions typically involve reacting a hydrocarbon with oxygen and ammonia in the presence of a catalyst to form a nitrile. Examples include the conversion of propane or propylene to acrylonitrile, and isobutane or isobutylene to methacrylonitrile.

A problem with each of these reactions is that they are exothermic and are typically conducted in fixed bed reactors where hot spots tend to form. The formation of these hot spots lowers selectivity towards the desired main product in favor of parallel reactions that form undesired products such as carbon oxides (i.e., CO, $CO_2$). The present invention provides a solution to this problem by conducting the reaction in a microchannel reactor wherein the tendency to form hot spots is reduced and selectivity to the desired product is enhanced. Enhanced selectivity with the inventive process is believed to be due at least in part to the fact that the microchannel reactor provides enhanced heat transfer characteristics and more precise control of residence times. Also, the internal dimensions of the microchannel reactor can be set at a level equal to or below the quench diameter for unwanted reactions.

With the inventive process it is possible to obtain relatively high heat and mass transfer rates and shorter contact times as compared to prior art processes wherein microchannel reactors are not used. This provides for more precise temperature control as compared to such prior art. This, in turn, leads to reduced peak temperatures and a reduction in the formation of undesired by-products. With this process, it is possible to obtain relatively high levels of conversion of the hydrocarbon reactant and high levels of selectivity to the desired product as compared to such prior art.

SUMMARY OF THE INVENTION

This invention relates to a process for converting a hydrocarbon reactant to a product comprising an oxygenate or a nitrile, the process comprising:
(A) flowing a reactant composition comprising the hydrocarbon reactant, and oxygen or a source of oxygen, and optionally ammonia, through a microchannel reactor in contact with a catalyst to convert the hydrocarbon reactant to the product, the hydrocarbon reactant undergoing an exothermic reaction in the microchannel reactor;
(B) transferring heat from the microchannel reactor to a heat exchanger during step (A); and
(C) quenching the product from step (A).

BRIEF DESCRIPTION OF THE DRAWINGS

In the annexed drawings, like parts and features have like designations.

DETAILED DESCRIPTION OF THE INVENTION

Figure 1:
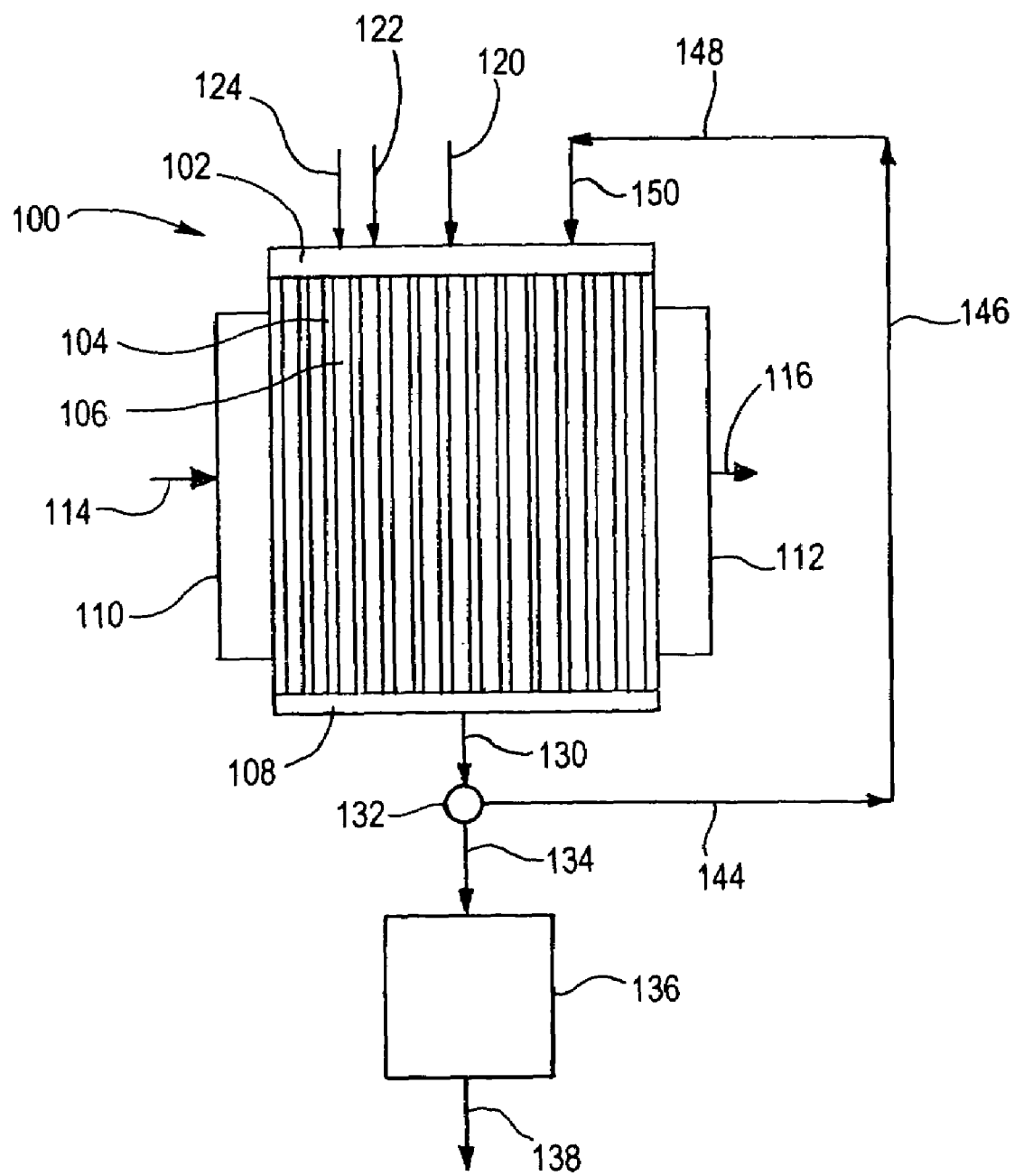
FIG. 1 is a schematic flow sheet illustrating the inventive process in a particular form wherein a fluid hydrocarbon reactant is converted to an oxygenate or nitrile in a microchannel reactor.

The term "microchannel" refers to a channel having at least one internal dimension of height or width (wall-to-wall, not counting catalyst) of up to about 10 millimeters (mm), and in one embodiment up to about 5 mm, and in one embodiment up to about 2 mm, and in one embodiment up to about 1 mm. In one embodiment, the height or width is in the range of about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.75 mm, and in one embodiment about 0.05 to about 0.5 mm. Both height and width are perpendicular to the direction of flow through the microchannel.

The term "adjacent" when referring to the position of one channel relative to the position of another channel means directly adjacent such that a wall separates the two channels. This wall may vary in thickness. However, "adjacent" channels are not separated by an intervening channel that would interfere with heat transfer between the channels.

The term "fluid" refers to a gas, a liquid, or a gas or a liquid containing dispersed solids, or a mixture thereof. The fluid may be in the form of a gas containing dispersed liquid droplets.

The term "contact time" refers to the volume of the reaction zone within the microchannel reactor divided by the volumetric feed flow rate of the reactant composition at a temperature of 0° C. and a pressure of one atmosphere.

The term "residence time" refers to the internal volume of a space (e.g., the reaction zone within a microchannel reactor) occupied by a fluid flowing through the space divided by the average volumetric flowrate for the fluid flowing through the space at the temperature and pressure being used.

The term "reaction zone" refers to the space within the microchannel reactor wherein the reactants contact the catalyst.

The term "conversion of hydrocarbon reactant" refers to the hydrocarbon reactant mole change between the reactant composition and the product divided by the moles of the hydrocarbon reactant in the reactant composition.

The term "selectivity to desired product" refers to the moles of the desired oxygenate or nitrile produced divided by the moles of the desired oxygenate or nitrile produced plus moles of other products (e.g., CO, $CO_2$) produced multiplied by their respective stoichiometric factors. For example, for the oxidation of ethylene to ethylene oxide with carbon dioxide as an unwanted side product, the production of one mole of ethylene oxide and one mole of carbon dioxide would correspond to a selectivity of $100 \times (1/(1+0.5)) = 67\%$.

The term "hydrocarbon" denotes a compound having a hydrocarbon or predominantly hydrocarbon character. These hydrocarbon compounds include the following:

(1) Purely hydrocarbon compounds; that is, aliphatic compounds, (e.g., alkane or alkylene), alicyclic compounds (e.g., cycloalkane, cycloalkylene), aromatic compounds, aliphatic- and alicyclic-substituted aromatic compounds, aromatic-substituted aliphatic compounds and aromatic-substituted alicyclic compounds, and the like. Examples include methane, ethane, ethylene, propane, propylene, ethyl cyclohexane, toluene, the xylenes, ethyl benzene, styrene, etc.

(2) Substituted hydrocarbon compounds; that is, hydrocarbon compound containing non-hydrocarbon substituents which do not alter the predominantly hydrocarbon character of the compound. Examples of the non-hydrocarbon substituents include hydroxy, acyl, nitro, etc.

(3) Hetero substituted hydrocarbon compounds; that is, hydrocarbon compounds which, while predominantly hydrocarbon in character, contain atoms other than carbon in a chain or ring otherwise composed of carbon atoms. Suitable hetero atoms include, for example, nitrogen, oxygen and sulfur.

The term "oxygenate" refers to a hydrocarbon product containing at least one oxygen atom; CO and $CO_2$ are excluded. Examples include alcohols (e.g., methanol, ethyl alcohol), epoxides (e.g., ethylene oxide), aldehydes (e.g., formaldehyde, acrolein), carboxylic acids (e.g., acetic acid, acrylic acid), carboxylic acid anhydrides (e.g., maleic anhydride), esters (e.g., vinyl acetate), and the like.

The term "quench" refers to a process by which a chemical reaction is terminated or substantially terminated using a rapid reduction in temperature of the reactants, a rapid introduction of a reactant or non-reactant fluid into the reactant mixture, or flowing the reactants through a restricted opening or passageway having a dimension at or below the quench diameter.

The term "quench diameter" refers to the internal dimension (e.g., height, width, diameter) of an opening or passageway for the reactants to flow through below which the reaction terminates or substantially terminates.

The inventive process will be described initially with reference to FIG. 1. Referring to FIG. 1, microchannel reactor 100 is comprised of a header 102, a plurality of process microchannels 104 which contain a catalyst 106 and operate in parallel, and a footer 108. The header 102 provides a passageway for fluid to flow into the process microchannels 104 with an even or substantially even distribution of flow to the process microchannels. The footer 108 provides a passageway for fluid to flow from the process microchannels 104 in a rapid manner with a relatively high rate of flow.

There is practically no upper limit to the number of process microchannels 104 that may be used in microchannel reactor 100. For example, the microchannel reactor 100 may contain one, two, three, four, five, six, eight, ten, twenty, fifty, one hundred, hundreds, one thousand, thousands, ten thousand, tens of thousands, one hundred thousand, hundreds of thousands, millions, etc., of the process microchannels 104. These process microchannels may be arranged in parallel, for example, in arrays of planar microchannels. The microchannel reactor may be of the microcomponent sheet architecture variety such as disclosed in U.S. Pat. No. 6,200,536B1, which is incorporated herein by reference. Each of the process microchannels 104 may have at least one internal dimension of height or width of up to about 10 mm, and in one embodiment from about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. The other internal dimension of height or width may be of any value, for example, it may range from about 0.1 cm to about 100 cm, and in one embodiment from about 0.1 to about 75 cm, and in one embodiment from about 0.1 to about 50 cm, and in one embodiment about 0.2 cm to about 25 cm. The length of each of the process microchannels 104 may be of any value, for example, it may range from about 1 cm to about 500 cm, and in one embodiment 1 cm to about 250 cm, and in one embodiment 1 cm to about 100 cm, and in one embodiment 1 cm to about 50 cm, and in one embodiment about 2 to about 25 cm.

In one embodiment, the process microchannels 104 contain a bulk flow path. The term "bulk flow path" refers to an open path (contiguous bulk flow region) within the process microchannels. A contiguous bulk flow region allows rapid fluid flow through the microchannels without large pressure drops. In one embodiment, the flow of fluid in the bulk flow region is laminar. Bulk flow regions within each process microchannel may have a cross-sectional area of about 0.05 to about 10,000 $mm^2$, and in one embodiment about 0.05 to about 5000 $mm^2$, and in one embodiment about 0.1 to about 2500 $mm^2$, and in one embodiment about 0.2 to about 1000 $mm^2$, and in one embodiment about 0.3 to about 500 $mm^2$, and in one embodiment about 0.4 to about 250 $mm^2$, and in one embodiment about 0.5 to about 125 $mm^2$. The bulk flow regions may comprise from about 5% to about 95%, and in one embodiment about 30% to about 80% of the cross-section of the process microchannels 104.

The header 102, footer 108 and the process microchannels 104 may be made of any material that provides sufficient strength, dimensional stability and heat transfer characteristics to permit operation of the inventive process. These materials include steel (e.g., stainless steel, carbon steel, and the like); monel; inconel; aluminum, titanium; nickel, platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

The reactant composition that flows into the microchannel reactor 100 comprises a hydrocarbon reactant, oxygen or a source of oxygen, and optionally ammonia. The hydrocarbon reactant flows through line 120 into header 102. The oxygen or oxygen source flows through line 122 into header 102. When used, the ammonia flows through line 124 into header 102. The reactant composition is mixed in header 102 and flows through process microchannels 104 in contact with catalyst 106. Alternatively, the reactants may be mixed in the process microchannels 104 using mixers disposed within the process microchannels. In one embodiment, a microchannel mixer feeding reactants into the header 102 may be useful. With such a microchannel mixer, adjacent microchannels in the mixer contain the different reactants which mix rapidly on leaving their respective microchannels in the header region. Optionally, one or more of the reactants (e.g., the oxygen or oxygen source) may be added to the main reactant flow at different points along the length of microchannel to control the heat release along the length of the microchannel. Within the process microchannels 104 the reactant composition undergoes an exothermic reaction resulting in the formation of the product. The product flows through the process microchannels 104 into footer 108. The product flows from footer 108 through line 130 to valve 132, through valve 132 to line 134, and from line 134 to quenching apparatus 136 wherein the product is quenched. The quenched product exits quenching apparatus 136 through line 138. In one embodiment, the quenched product exiting quenching apparatus 136 flows through a second quenching apparatus or stage without flowing through an intermediate valve.

Optionally, the product and unreacted parts from the reactant composition may be further processed in a second microchannel reactor that is similar in design and operation to microchannel reactor 100, or they may be recycled from valve 132 to line 144, through line 144 to line 146, through line 146 to line 148, through line 148 to line 150, and through line 150 into the microchannel reactor 100. In one embodiment, the desired product may be separated from the unreacted parts of the reactant composition using known techniques, and the unreacted parts may be further processed in a second microchannel reactor similar in design and operation to the microchannel reactor 100 or they may be recycled back to the microchannel reactor 100 as described above. However, an advantage of the inventive process is that it is possible to obtain a relatively high level of conversion of the hydrocarbon reactant in a single cycle or a single pass through the microchannel reactor, that is, without the foregoing recycle step or further processing in a second reactor.

During the inventive process, the reaction within the process microchannels 104 is exothermic and the microchannel reactor 100 is cooled using a heat exchanger in thermal contact with the process microchannels 104. The heat exchanger may be in the form of heat exchange channels (not shown in the drawings) adjacent to the process microchannels 104. The heat exchange channels may be microchannels. A heat exchange fluid flows from heat exchange header 110 through the heat exchange channels to heat exchange footer 112. The heat exchange channels may be aligned to provide a flow in a cross-current direction relative to the process microchannels 104 as indicated by arrows 114 and 116. The process microchannels 104 transfer heat to the heat exchange channels. The heat exchange fluid may be recirculated using known techniques. Alternatively, the heat exchange channels may be oriented to provide for flow of the heat exchange fluid in a cocurrent or counter current direction relative to the direction of the flow of fluid through the process microchannels 104.

Each of the heat exchange channels may have at least one internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The other internal dimension may range from about 1 mm to about 1 m, and in one embodiment about 1 mm to about 0.5 m, and in one embodiment about 2 mm to about 10 cm. The length of the heat exchange channels may range from about 1 mm to about 1 m, and in one embodiment about 1 cm to about 0.5 m. The separation between each process microchannel 104 and the next adjacent heat exchange channel may range from about 0.05 mm to about 5 mm, and in one embodiment about 0.2 mm to about 2 mm.

The heat exchange channels may be made of any material that provides sufficient strength, dimensional stability and heat transfer characteristics to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

The heat exchange fluid may be any fluid. These include air, steam, liquid water, gaseous nitrogen, liquid nitrogen, other gases including inert gases, carbon monoxide, molten salt, oils such as mineral oil, and heat exchange fluids such as Dowtherm A and Therminol which are available from Dow-Union Carbide.

The heat exchange fluid may comprise one or more of the reactant streams. This can provide process pre-heat and increase overall thermal efficiency of the process.

In one embodiment, the heat exchange channels comprise process channels wherein an endothermic reaction is conducted. These heat exchange process channels may be microchannels. Examples of endothermic reactions that may be conducted in the heat exchange channels include steam reforming and dehydrogenation reactions. A typical heat flux for convective cooling in a microchannel reactor is on the order of about 1 to about 10 W/cm$^2$. The incorporation of a simultaneous endothermic reaction to provide an improved heat sink may enable a typical heat flux of roughly an order of magnitude above the convective cooling heat flux.

In one embodiment, the heat exchange fluid undergoes a phase change as it flows through the heat exchange channels. This phase change provides additional heat removal from the process microchannels beyond that provided by convective cooling. For a liquid heat exchange fluid being vaporized, the additional heat being transferred from the process microchannels would result from the latent heat of vaporization required by the heat exchange fluid. An example of such a phase change would be an oil or water that undergoes boiling.

The added cooling of the process microchannels 104 provided by step (B) of the inventive process is essential to controlling selectivity towards the main or desired product due to the fact that such added cooling reduces or eliminates the formation of undesired by-products from undesired parallel reactions with higher activation energies. As a result of this added cooling, in one embodiment, the temperature of the reactant composition at the entrance to the process microchannels 104 may be within (plus or minus) about 200° C., and in one embodiment within about 150° C., and in one embodiment within about 100° C., and in one embodiment within about 50° C., and in one embodiment within about 25° C., and in one embodiment within about 10° C., of the temperature of the product (or mixture of product and unreacted reactants) at the exit of the process microchannels. In one embodiment, the reaction within the process microchannels 104 is conducted under isothermal or near isothermal conditions as a result of such added cooling.

The microchannel reactor 100 may be made using known techniques. These include laminating interleaved shims, where shims designed for the process microchannels 104 are interleaved with shims designed for the heat exchange channels.

The quenching apparatus 136 may comprise a heat exchange apparatus capable of reducing the temperature of the product flowing from the microchannel reactor by up to about 950° C. within a period of up to about 500 milliseconds (ms). The temperature may be reduced by up to about 50° C., and in one embodiment up to about 100° C., and in one embodiment up to about 250° C., and in one embodiment up to about 500° C., and in one embodiment up to about 750° C., within a time period of up to about 500 ms, and in one embodiment up to about 400 ms, and in one embodiment up to about 300 ms, and in one embodiment up to about 200 ms, and in one embodiment up to about 100 ms, and in one embodiment up to about 50 ms, and in one embodiment up to about 35 ms, and in one embodiment up to about 20 ms, and in one embodiment up to about 15 ms, and in one embodiment up to about 10 ms, and in one embodiment within a time period of up to about 5 ms. In one embodiment, the temperature is reduced by up to about 500° C. within a time period of about 5 to about 100 ms, and in one embodiment about 10 to about 50 ms. The quenching apparatus may be integral with the microchannel reactor, or it may be separate from the microchannel reactor. The quenching apparatus may comprise a microchannel heat exchanger. The quenching apparatus may comprise a heat exchanger that is adjacent to or interleaved with the product stream exiting the microchannel reactor. The quenching apparatus may comprise a mixer capable of rapidly mixing the product with a secondary cooling fluid. The secondary cooling fluid may be a low temperature steam or a condensable hydrocarbon injected as a liquid.

Alternatively, the quenching apparatus may comprise a narrow gap or passageway for the reactants to flow through, the gap or passageway having a dimension equal to or below the quench diameter for the reaction. In this embodiment, the reaction terminates as the reactants flow through the gap or passageway as a result of wall collisions. The gap or passageway may have a height or width of up to about 5 mm, and in one embodiment up to about 3 mm, and in one embodiment up to about 1 mm, and in one embodiment up to about 0.5 mm, and in one embodiment up to about 0.1 mm, and in one embodiment up to about 0.05 mm. This quenching apparatus may comprise a microchannel or a plurality of parallel microchannels. This quenching apparatus may comprise part of the process microchannels used with the inventive process downstream of the catalyst contained within the microchannels. The narrow gap or passageway may be used in conjunction with one or more of the other quenching apparatuses (e.g., heat exchangers) discussed above.

Figure 2:
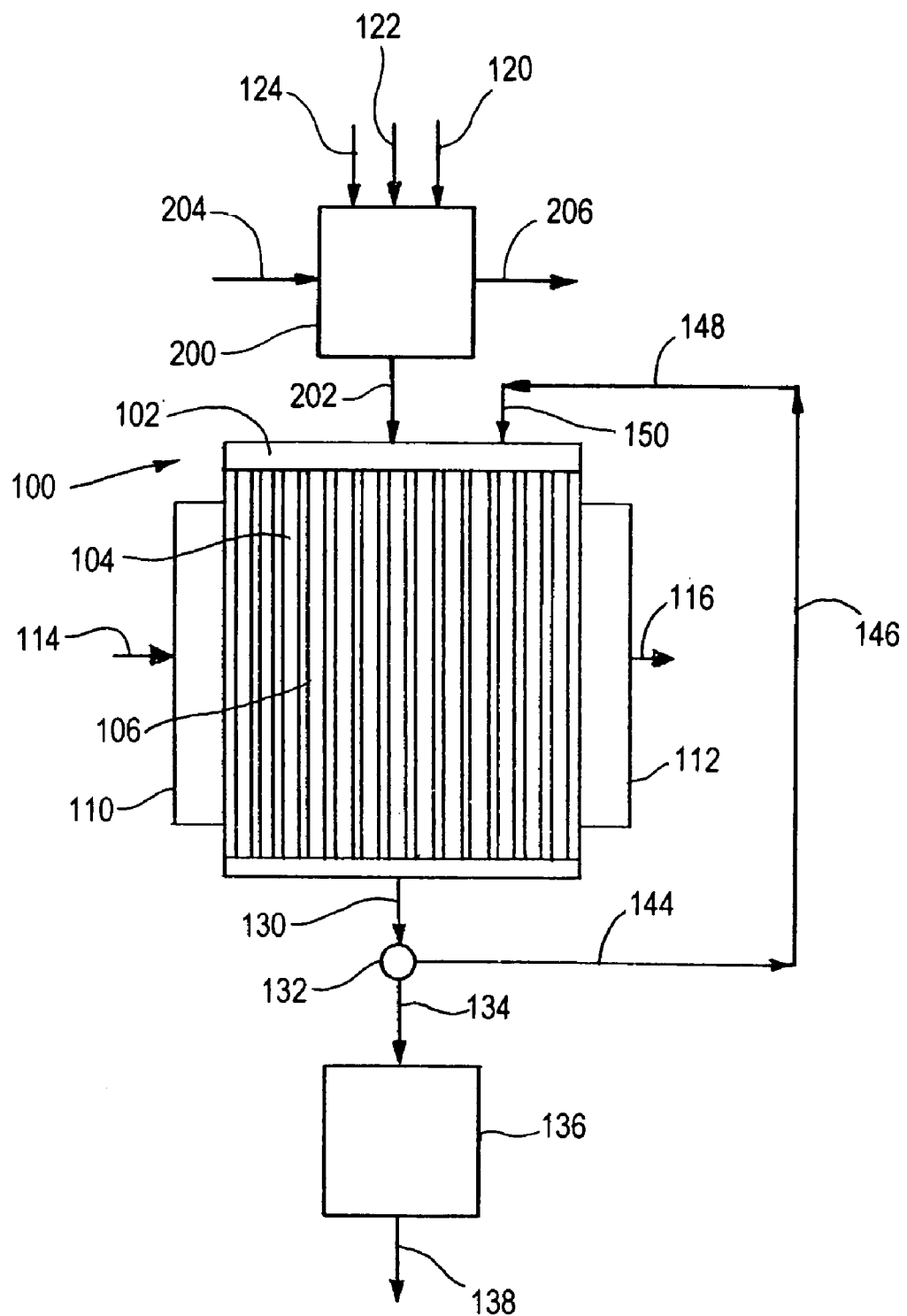
FIG. 2 is a schematic flow sheet illustrating an alternate embodiment of the inventive process.

The process illustrated in FIG. 2 is the same as illustrated in FIG. 1 with the exception that premixing and preheating apparatus 200 has been added upstream of the microchannel reactor 100. The premixing and preheating apparatus may comprise a microchannel mixer that is separate from or integral with the microchannel reactor 100. The hydrocarbon reactant enters the premixing and preheating apparatus 200 through line 120. The oxygen or oxygen source enters premixing and preheating apparatus 200 through line 122. When used the ammonia enters premixing and preheating apparatus 200 through line 124. The premixing and preheating apparatus 200 may be of any conventional design and may be heated using a heat exchange fluid flowing through the apparatus 200 as indicated by arrows 204 and 206. Within the premixing and preheating apparatus 200, the hydrocarbon reactant, the oxygen or oxygen source and when used the ammonia are mixed and heated to the temperature desired for entry into the process microchannels 104. The premixed and preheated reactant composition flows from premixing and preheating apparatus 200 through line 202 to header 102. From header 102 the reactant composition flows through microchannels 104 in contact with catalyst 106, and undergoes an exothermic reaction resulting in the formation of the desired product. The product flows into the footer 108, and from the footer 108 through line 130 to valve 132, through valve 132 to line 134, through line 134 to quench apparatus 136 wherein the product is quenched. The quenched product exits quench apparatus 136 through line 138. Optionally, the unreacted parts of the reactant composition, and optionally the product, may be further processed in a second microchannel reactor or recycled from valve 132 to line 144, through line 144 to line 146, through line 146 to line 148, through line 148 to line 150, and through line 150 into microchannel reactor 100, as discussed above.

The premixing and preheating apparatus 200 may comprise any mixing apparatus capable of mixing the hydrocarbon reactant, oxygen or oxygen source, and optionally ammonia, and heating the resulting reactant composition to the temperature desired for entry into the microchannel reactor 100. The reactant composition may be heated to a temperature in the range of about 200° C. to about 800° C., and in one embodiment about 300° C. to about 700° C., and in one embodiment about 400° C. to about 600° C. Examples of the mixers that may be used include microchannel mixers, gas ejectors, concentric nozzles, jets, and the like. The mixing may be effected by flowing the reactants into a porous material such as a foam, felt, wad or bed of particulates made of any suitable material, including ceramics, quartz and high temperature metals and alloys such as Inconel, FeCrAlY, and the like.

Figure 3A:
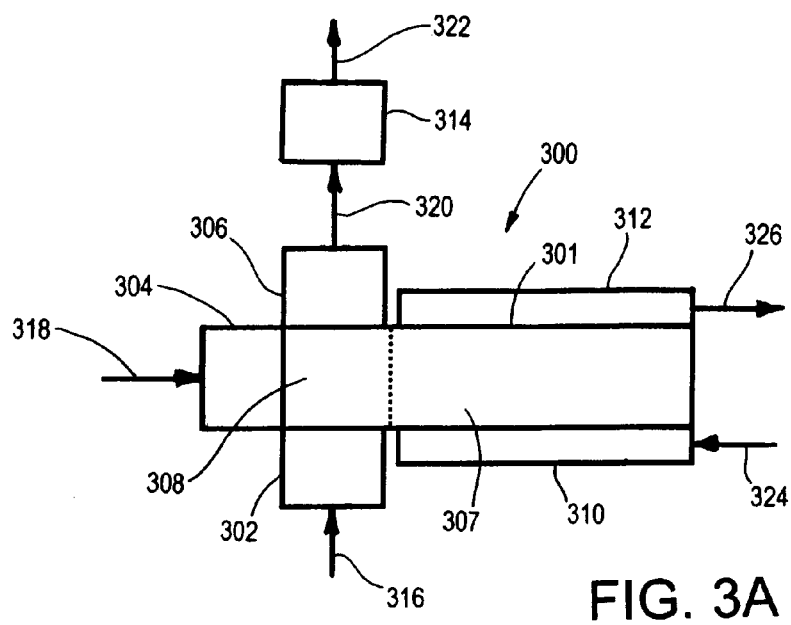
FIG. 3A is a schematic flow sheet illustrating another alternate embodiment of the inventive process.
Figure 3B:
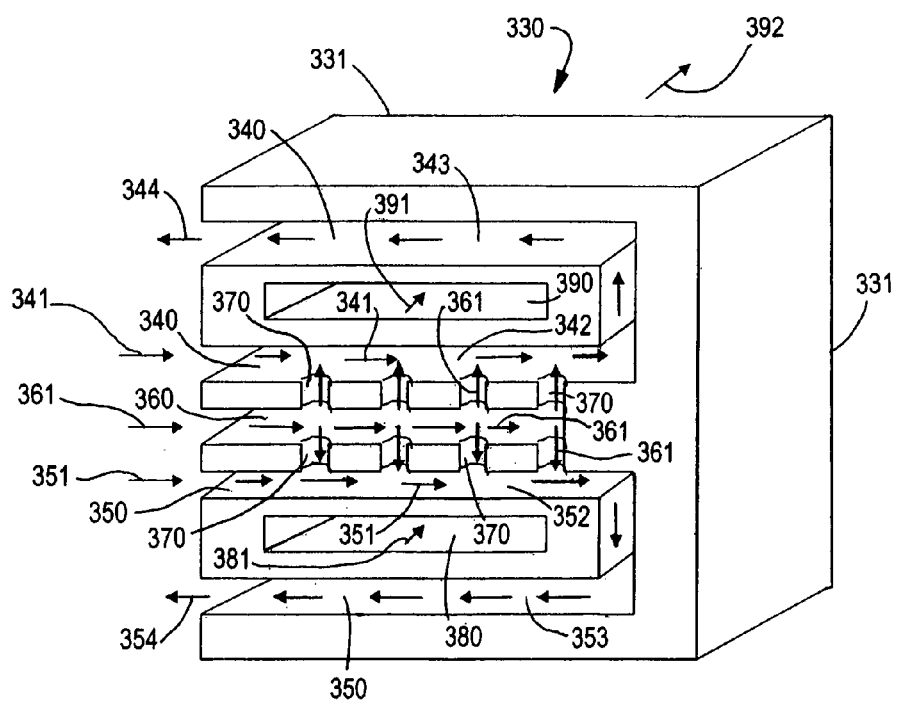
FIG. 3B is a schematic flow sheet illustrating the operation of a particular form of a microchannel reactor used with the inventive process.

The inventive process may be conducted as illustrated in FIGS. 3A and 3B. Referring to FIG. 3A, the process is operated using microchannel reactor 300 which includes microchannel reactor core 301, reactant header 302, oxidant header 304, product footer 306, heat exchange header 310, heat exchange footer 312, and quenching apparatus 314. The microchannel reactor core 301 includes reactor zone 307, and manifold and recuperator 308. The reactant composition comprising the hydrocarbon reactant, and optionally ammonia, flows into the microchannel reactor 300 through the reactant header 302 as indicated by directional arrow 316. The oxygen or source of oxygen flows into the microchannel reactor 300 through the oxidant header 304 as indicated by directional arrow 318. The hydrocarbon reactant, oxygen or source of oxygen, and optionally ammonia, flow into and through the manifold and recuperator 308 into the reactor zone 307 wherein they contact a catalyst and react to form the desired product. The product flows from the reactor zone 307 through the manifold and recuperator 308 to product footer 306, and from product footer 306 through the quenching apparatus 314 as indicated by directional arrows 320 and 322. A heat exchange fluid flows into heat exchange header 310, as indicated by directional arrow 324, and from heat exchange header 310 through microchannel reactor 301 to heat exchange footer 312, and out of heat exchange footer 312, as indicated by directional arrow 326. Within the microchannel reactor core 301, the oxygen or source of oxygen is added to the hydrocarbon reactant, and optionally ammonia, using staged addition. This is illustrated in FIG. 3B.

Referring to FIG. 3B, which illustrates repeating unit 330 which is used in the microchannel reactor 300 illustrated in FIG. 3A, and is housed within housing unit 331. The inventive process is conducted using process microchannels 340 and 350, oxidant microchannel 360, orifices 370, and heat exchange microchannels 380 and 390. The hydrocarbon reactant, and optionally ammonia, flows through process microchannels 340 and 350, as indicated by the directional arrows 341 and 351, respectively. Oxygen or a source of oxygen flows through oxidant microchannel 360 into orifices 370, as indicated by directional arrows 361. The oxygen or oxygen source mixes with the hydrocarbon reactant, and optionally ammonia, in the process microchannels 340 and 350. The process microchannels 340 and 350 have reaction zones 342 and 352, respectively, wherein the catalyst 106 is present and the reactants contact the catalyst and undergo reaction, and channel zones 343 and 353, respectively, wherein further contact with the catalyst may be effected or product cooling and/or quenching may be effected. Within the process microchannels 340 and 350, the reactants contact the catalyst and react to form the desired product. The product exits the process microchannels 340 and 350, as indicated by the directional arrows 344 and 354, respectively. The product exiting the process microchannels 340 and 350 flows to the manifold and recuperator 308, and from the manifold and recuperator 308 through the product footer 306 to the quenching apparatus 314, as indicated above. The quenched product exits the quenching apparatus 314, as indicated by directional arrow 322. Heat exchange fluid flows from header 310 through heat exchange channels 380 and 390, as indicated by directional arrows 381, and 391 and 392, respectively, to heat exchange footer 312. The repeating unit 330 illustrated in FIG. 3B may occur once within the microchannel reactor 300 or it may be repeated any number of times, for example, two, three, four, five, ten, twenty, fifty, one hundred, hundreds, one thousand, thousands, ten thousand, tens of thousands, one hundred thousand, hundreds of thousands or millions of times. The staged oxygen addition provided for in this process provides the advantage of lowering local oxygen pressure and favoring desired lower-order partial oxidation reactions over higher-order competing and undesired combustion reactions.

Each of the process microchannels 340 and 350 and the oxidant microchannel 360 may have at least one internal dimension of height or width of up to about 10 mm, and in one embodiment from about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. The other internal dimension of height or width may be of any value, for example, it may range from about 0.1 cm to about 100 cm, and in one embodiment from about 0.1 to about 75 cm, and in one embodiment from about 0.1 to about 50 cm, and in one embodiment about 0.2 cm to about 25 cm. The length of each of the process microchannels 340 and 350, and the oxidant microchannel 360, may be of any value, for example, the lengths may range from about 1 cm to about 500 cm, and in one embodiment 1 cm to about 250 cm, and in one embodiment 1 cm to about 100 cm, and in one embodiment 1 cm to about 50 cm, and in one embodiment about 2 to about 25 cm.

Each of the heat exchange channels 380 and 390 may have at least one internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The other internal dimension may range from about 1 mm to about 1 m, and in one embodiment about 1 mm to about 0.5 m, and in one embodiment about 2 mm to about 10 cm. The length of the heat exchange channels may range from about 1 mm to about 1 m, and in one embodiment about 1 cm to about 0.5 m. These heat exchange channels may be microchannels. The separation between each process microchannel 340 or 350 and the next adjacent heat exchange channel 380 or 390 may range from about 0.05 mm to about 5 mm, and in one embodiment about 0.2 mm to about 2 mm.

The housing 301, process microchannels 340 and 350, oxidant microchannel 360, and heat exchange channels 380 and 390 may be made of any material that provides sufficient strength, dimensional stability and heat transfer characteristics to permit operation of the inventive process. These materials include steel (e.g., stainless steel, carbon steel, and the like); monel; inconel; aluminum, titanium; nickel, platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

Alternatively, the staged addition of the oxygen or source of oxygen to the microchannel reactor may be effected using separate devices, through the use of small orifices or jets within one device, or from a microporous membrane or alternate sparging sheet. The staged addition of oxygen to partial oxidation reactions, and specifically oxidative dehydrogenation reactions, is disclosed in Tonkovich, Zilka, Jimenz, Roberts, and Cox, 1996, "Experimental Investigations of Inorganic Membrane Reactors: a Distributed Feed Approach for Partial Oxidation Reactions," Chemical Engineering Science, 51(5), 789-806), which is incorporated herein by reference.

Figure 4:
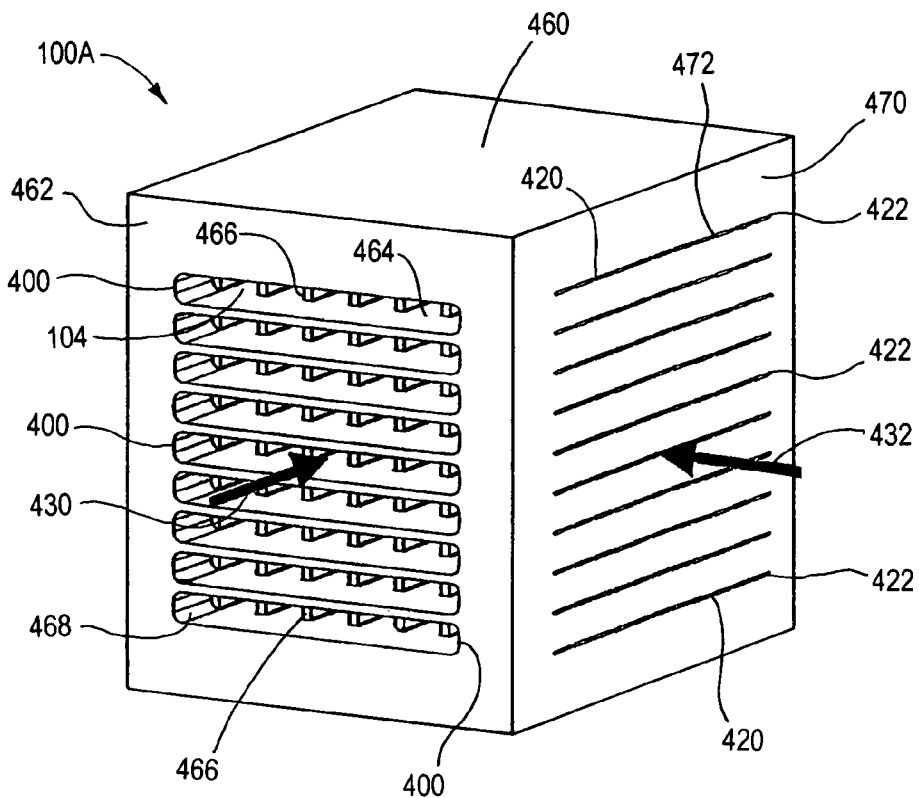
FIG. 4 is a schematic illustration of a cross flow reactor embodying a particular form of a microchannel reactor for conducting the inventive process.

The inventive process may be conducted in microchannel reactor 100A which is illustrated in FIG. 4. Referring to FIG. 4, microchannel reactor 100A contains an array of process microchannels 104 which extend parallel to each other and are arranged in rows 400. The rows 400 are positioned in separate planes one above another. The microchannel reactor 100A also contains an array of heat exchange microchannels 420 extending parallel to each other and arranged in rows 422. The rows 422 of heat exchange microchannels 420 are positioned in separate planes one above another. The heat exchange microchannels 420 extend transversely of and in thermal contact with the process microchannels 104. The rows 422 of heat exchange microchannels 420, and the rows 400 of process microchannels 104 are positioned in separate alternating planes one above another.

The microchannel reactor 100A contains nine rows 400 of process channels 104, with six process microchannels 104 in each row 400 for a total of 54 process microchannels 104. It is to be understood, however, that the microchannel reactor 100A may contain any number of process microchannels 104, for example, hundreds, thousands, tens of thousands, hundreds of thousands, or millions of process microchannels 104. Similarly, the microchannel reactor 100A contains 10 rows 422 of heat exchange microchannels 420. Each row 422 contains 11 heat exchange microchannels 420 for a total of 110 heat exchange microchannels 420. It is to be understood, however, that although the illustrated microchannel reactor contains a total of 110 heat exchange microchannels 420, additional heat exchange microchannels 420, for example, thousands, tens of thousands, hundreds of thousands, or millions of heat exchange microchannels 420 may be employed with the microchannel reactor 100A.

The process microchannels 104 in microchannel reactor 100A have cross sections in the form of squares or rectangles. The smallest internal dimension for each process microchannel 104, whether it be height or width, may be up to about 10 mm, and in one embodiment from about 0.05 to about 10 mm, and in one embodiment from about 0.05 to about 5 mm, and in one embodiment about 0.05 to about 2 mm, and in one embodiment about 0.05 to about 1.5 mm. The other internal dimension of height or width may be in the range of about 0.1 to about 100 cm, and in one embodiment about 0.2 to about 25 cm. The length of each process microchannel 104 may be from about 1 to about 500 cm, and in one embodiment about 1 to about 250 cm, and in one embodiment about 1 to about 100 cm, and in one embodiment about 1 to about 50 cm, and in one embodiment about 2 to about 25 cm.

Each heat exchange microchannel 420 may have a cross section in the form of a square, rectangle, triangle, diamond, circle or elipse and has a width or height of about 0.025 to about 10 mm, and in one embodiment about 0.05 to about 5 mm, and in one embodiment about 0.1 to about 2 mm. The length of each heat exchange microchannel 420 may range from about 1 mm to about 1 meter, and in one embodiment about 1 cm to about 0.5 meter.

The separation between each row 422 of heat exchange microchannels 420 and the next adjacent row 400 of process microchannels 104 may range from about 0.05 to about 10 mm, and in one embodiment about 0.1 to about 5 mm, and in one embodiment about 0.1 to about 2 mm.

During the operation of the inventive process, the reactant composition and product flow through the process microchannels 104 in the direction indicated by arrow 430. The catalyst 106 is contained within the process microchannels 104. A heat exchange fluid flows through the heat exchange microchannels 420 in the direction indicated by arrow 432.

The microchannel reactor 100A may be constructed of any material that provides sufficient strength, dimensional stability and heat transfer characteristics for carrying out the inventive process. Examples of suitable materials include steel (e.g., stainless steel, carbon steel, and the like), aluminum, titanium, nickel, and alloys of any of the foregoing metals, plastics (e.g., epoxy resins, UV cured resins, thermosetting resins, and the like), monel, inconel, ceramics, glass, composites, quartz, silicon, or a combination of two or more thereof. The microchannel reactor 100A may be fabricated using known techniques including wire electrodischarge machining,conventional machining, laser cutting, photochemical machining, electrochemical machining, molding, water jet, stamping, etching (for example, chemical, photochemical or plasma etching) and combinations thereof. The microchannel reactor 100A may be constructed by forming layers or sheets with features removed that allow flow passages. A stack of sheets may be assembled via diffusion bonding, laser welding, diffusion brazing, and similar methods to form an integrated device. The microchannel reactor 100A has appropriate headers, footers, valves, conduit lines, etc. to control input of the reactants, output of the product, and flow of the heat exchange fluid. These are not shown in FIG. 4, but can be readily provided by those skilled in the art.

The reactant composition may be in the form of a fluid. This fluid may be a liquid or a gas, and in one embodiment it is in the form of a gas. This fluid may be in the form of a gas containing dispersed liquid droplets. The reactant composition comprises at least one hydrocarbon reactant.

The purity of the reactant composition is not critical, though it is desirable to avoid the presence of compounds which may poison the catalyst. As a result, the reactant composition may further comprise impurities such as air, carbon dioxide, and the like.

The reactant composition may include a diluent material. Examples of such diluents include nitrogen, helium, carbon dioxide, liquid water, steam, and the like. The volume ratio of diluent to hydrocarbon reactant in the reactant composition may range from zero to about 80% by volume, and in one embodiment from zero to about 50% by volume. However, an advantage of at least one embodiment of the invention is that it is possible to conduct the inventive process without the use of such diluents, thus a more efficient and compact process may be provided.

The hydrocarbon reactant may comprise any hydrocarbon compound that is capable of undergoing an oxidation or ammoxidation reaction, and is a fluid (and in one embodiment a vapor) at the temperature and pressure used within the process microchannels. Examples include saturated aliphatic compounds (e.g., alkanes), unsaturated aliphatic compounds (e.g., monoenes, polyenes, and the like), aldehydes, alkyl substituted aromatic compounds, alkylene substituted aromatic compounds, and the like.

The saturated aliphatic compounds include alkanes containing 1 to about 20 carbon atoms per molecule, and in one embodiment 1 to about 18 carbon atoms, and in one embodiment 1 to about 16 carbon atoms, and in one embodiment 1 to about 14 carbon atoms, and in one embodiment 1 to about 12 carbon atoms, and in one embodiment 1 to about 10 carbon atoms, and in one embodiment 1 to about 8 carbon atoms, and in one embodiment 1 to about 6 carbon atoms, and in one embodiment 1 to about 4 carbon atoms. These include methane, ethane, propane, isopropane, butane, isobutane, the pentanes, the hexanes, the heptanes, the octanes, the nonanes, the decanes, and the like.

The unsaturated aliphatic compounds include alkenes or alkylenes containing 2 to about 20 carbon atoms, and in one embodiment 2 to about 18 carbon atoms, and in one embodiment 2 to about 16 carbon atoms, and in one embodiment 2 to about 14 carbon atoms, and in one embodiment 2 to about 12 carbon atoms, and in one embodiment 2 to about 10 carbon atoms, and in one embodiment 2 to about 8 carbon atoms, and in one embodiment 2 to about 6 carbon atoms per molecule, and in one embodiment 2 to about 4 carbon atoms. These include ethylene; propylene; 1-butene; 2-butene; isobutylene; 1-pentene;2-pentene; 3-methyl-1-butene; 2-methyl-2-butene; 1-hexene; 2,3-dimethyl-2-butene; 1-heptene; 1-octene; 1-nonene; 1-decene; and the like.

The unsaturated aliphatic compounds may comprise polyenes. These include dienes, trienes, and the like. These compounds may contain 3 to about 20 carbon atoms per molecule, and in one embodiment 3 to about 18 carbon atoms, and in one embodiment 3 to about 16 carbon atoms, and in one embodiment 3 to about 14 carbon atoms, and in one embodiment 3 to about 12 carbon atoms, and in one embodiment 3 to about 10 carbon atoms, and in one embodiment about 4 to about 8 carbon atoms, and in one embodiment about 4 to about 6 carbon atoms. Examples include 1,2-propadiene (also known as allene); 1,3-butadiene; 2-methyl-1,3-butadiene (also known as isoprene); 1,3-pentadiene; 1,4-pentadiene; 1,5-hexadiene; 2,4-hexadiene; 2,3-dimethyl-1,3-butadiene; and the like.

The aldehydes may be saturated or unsaturated. They may be aliphatic or aromatic. The aldehydes may contain 1 to about 20 carbon atoms per molecule, and in one embodiment 1 to about 18 carbon atoms, and in one embodiment 1 to about 16 carbon atoms, and in one embodiment 1 to about 14 carbon atoms, and in one embodiment 1 to about 12 carbon atoms, and in one embodiment 1 to about 10 carbon atoms, and in one embodiment 1 to about 8 carbon atoms, and in one embodiment about 2 to about 8 carbon atoms, and in one embodiment about 3 to about 6 carbon atoms. Examples include formaldehyde; acetaldehyde; propionaldehyde; n-butyraldehyde; n-valeraldehyde; caproaldehyde; acrolein; tran-2-cis-6-nonadienal; n-heptylaldehyde; trans-2-hexenal; hexadeconal; benzaldehyde; phenylacetaldehyde; o-tolualdehyde; m-tolualdehyde; p-tolualdehyde; salicylaldehyde; p-hydroxybenzaldehyde; and the like.

The alkyl or alkylene substituted aromatic compounds may contain one or more alkyl or alkylene substituents. These compounds may be monocyclic (e.g., phenyl) or a polycyclic (e.g., naphthyl). These compounds include alkyl substituted aromatic compounds containing one or more alkyl groups containing 1 to about 20 carbon atoms, and in one embodiment 1 to about 18 carbon atoms, and in one embodiment 1 to about 16 carbon atoms, and in one embodiment 1 to about 14 carbon atoms, and in one embodiment 1 to about 12 carbon atoms, and in one embodiment 1 to about 10 carbon atoms, and in one embodiment 1 to about 8 carbon atoms, and in one embodiment about 2 to about 6 carbon atoms, and in one embodiment about 2 to about 4 carbon atoms. These also include the alkylene substituted aromatic compounds containing one or more alkylene groups containing 2 to about 20 carbon atoms, and in one embodiment 2 to about 18 carbon atoms, and in one embodiment 2 to about 16 carbon atoms, and in one embodiment 2 to about 14 carbon atoms, and in one embodiment 2 to about 12 carbon atoms, and in one embodiment 2 to about 10 carbon atoms, and in one embodiment 2 to about 8 carbon atoms, and in one embodiment about 2 to about 6 carbon atoms, and in one embodiment about 2 to about 4 carbon atoms. Examples include toluene, o-xylene, m-xylene, p-xylene, hemimellitene, pseudocumene, mesitylene, prehnitene, isodurene, durene, pentamethylbenzene, hexamethylbenzene, ethylbenzene, n-propylbenzene, cumene, n-butylbenzene, isobutylbenzene, sec-butylbenzene, tert-butylbenzene, p-cymene, styrene, and the like.

The oxygen or oxygen source may comprise molecular oxygen, air or other oxidants, such as nitrogen oxides, which can function as a source of oxygen. The oxygen source may be carbon dioxide, carbon monoxide or a peroxide (e.g., hydrogen peroxide). Gaseous mixtures containing oxygen, such as mixtures of oxygen and air, or mixtures of oxygen and an inert gas (e.g., helium, argon, etc.) or a diluent gas (e.g., carbon dioxide, water vapor, etc.) may be used. The mole ratio of the hydrocarbon reactant to oxygen may range from about 0.2:1 to about 8:1, and in one embodiment about 0.5:1 to about 4:1, and in one embodiment about 1:1 to about 3:1. In one embodiment, the mole ratio is about 2:1 or higher, and in one embodiment about 2.5:1 or higher. In one embodiment, the mole ratio is about 1.8 or less.

The ammonia may be obtained from any source. When used, the mole ratio of the hydrocarbon reactant to ammonia may range from about 0.5:1 to about 5:1, and in one embodiment about 0.5:1 to about 2:1.

The catalyst may comprise any catalyst that is useful as an oxidation or ammoxidation catalyst. The catalyst may comprise a metal, metal oxide or mixed metal oxide of a metal selected from Mo, W, V, Nb, Sb, Sn, Pt, Pd, Cs, Zr, Cr, Mg, Mn, Ni, Co, Ce, or a mixture of two or more thereof. These catalysts may also comprise one or more alkali metals or alkaline earth metals or other transition metals, rare earth metals, or lanthanides. Additionally elements such as P and Bi may be present. The catalyst may be supported, and if so, useful support materials include metal oxides (e.g., alumina, titania, zirconia), silica, mesoporous materials, zeolites, refractory materials, or combinations of two or more thereof.

The catalyst may comprise an oxidation catalyst represented by the formula $$Mo_{12}W_aBi_bFe_cCo_dNi_eSi_fK_gSn_hO_x$$

in which: a is between 0 and 5, b is between 0.5 and 5, c is between 0.1 and 10, d is between 0.5 and 10, e is between 0 and 10, f is between 0 and 15, g is between 0 and 1, h is between 0 and 2, and x is the quantity of oxygen bonded to the other elements and depends on their oxidation states. These catalysts are described in U.S. Pat. No. 6,251,821 B1 as being useful for making acrolein from propylene by oxidation. This patent is incorporated herein by reference.

The catalyst may comprise an oxidation catalyst represented by the formula $$Mo_aBi_bP_cX^1_dX^2_eX^3_fX^4_gO_h$$

wherein $X^1$ is V, Nb, Ta, Cr, W, Ga, Ce and/or La; $X^2$ is Li, Na, K, Rb, Cs, Cu, Ag, Au, Pd and/or Pt; $X^3$ is Sn, Pb, Sb, Bi, Te, Fe, Co and/or Ni; $X^4$ is Si, Al, Ti and/or Zr; a is 0 to 2; d is 0 to 2, with the proviso that the sum of a and d is at least 0.20; b is 0 to 1.5, c is 0 to 10, with the proviso that the sum of b and c is at least 0.1; e is 0 to 0.5, f is 0 to 0.5, g is 0 to 20 and h is a number different from zero which is determined by the valence and frequency of the elements different from oxygen. This catalyst is disclosed in U.S. Pat. No. 6,252,122 B1 as being useful for converting propane to acrolein. This patent is incorporated herein by reference.

The catalyst may comprise an oxidation catalyst represented by the formula $$Mo_{12}Bi_aFe_bX^1_cX^2_dX^3_eX^4_fO_n$$

where $X^1$ is Ni and/or Co; $X^2$ is Tl, an alkali metal and/or an alkaline earth metal; $X^3$ is Zn, P, As, B, Sb, Sn, Ce, Pb, and/or W; $X^4$ is Si, Al, Ti and/or Zr; a is from 0.5 to 5; b is from 0.01 to 5, and in one embodiment from 2 to 4; c is from 0 to 10, and in one embodiment from 3 to 10; d is from 0 to 2, and in one embodiment from 0.02 to 2; e is from 0 to 8, and in one embodiment from 0 to 5; f is from 0 to 10; and n is a number which is determined by the valency and frequency of the elements other than oxygen. These catalysts are disclosed in U.S. Pat. No. 6,395,936 B1 as being useful for the oxidation of propylene to acrolein. This patent is incorporated herein by reference.

The catalyst may comprise an oxidation catalyst represented by the formula $$[Bi_nA_aO_x][(100-z)\% \ E_eFe_fNi_gMo_mO_y+z\% \ SiO_2]$$

wherein A is at least one element selected from the group consisting of B, P and Mo; E is at least one element having the atomic valence of 2; when m is 1, n is 0.001 to 3, a is 0 to 3, e is 0 to 3, f is 0.01 to 5, g is 0.1 to 5, and z is 0 to 90; and x and y are numbers such that the valence requirements of the other elements for oxygen in the core and shell catalytic phase, respectively, are satisfied. This catalyst is disclosed in U.S. Pat. No. 6,410,800 B1 as being useful for the oxidation of propylene to acrolein. This patent is incorporated herein by reference.

The catalyst may comprise an oxidation catalyst represented by the formulae $$Mo_{12}Co_{3.5}Bi_{1.1}Fe_{0.8}W_{0.5}Si_{1.4}K_{0.05}O_x$$

or $$Ni_{2.1}Co_{3.5}Fe_{2.6}P_{0.43}Bi_{1.0}Mo_{9.3}Mn_{0.15}Cr_{0.09}Ba_{0.07}Zr_{0.0012}K_{0.07}O_x$$

where x is the quantity of oxygen bonded to the other elements and depends on their oxidation state. These catalysts are disclosed in U.S. Pat. No. 6,437,193 B1 as being useful for the oxidation of propylene to acrolein. This patent is incorporated herein by reference.

The catalyst may comprise an oxidation catalyst represented by the formula $$Bi_bMo_cV_vA_aD_dE_eO_x$$

wherein A is one or more of K, Na, Li, Cs and Tl; D is one or more of Fe, Ni, Co, Zn, Ce or La; E is one or more of W, Nb, Sb, Sn, P, Cu, Pb, B, Mg, Ca or Sr; a, d and e are each 0 to 10; b is 0.1 to 10; c is 0.1 to 20; v is 0.1 to 10; c:b is from 2:1 to 30:1; v:b is from 1.5 to 8:1; and x is determined by the frequency and the valence of the elements other than oxygen in the above formula. This catalyst is disclosed in U.S. Pat. No. 5,198,580 as being useful for the conversion of propane to acrylic acid, propylene, acrolein and acetic acid.

The catalyst may comprise an oxidation catalyst represented by the formula $$M^1{}_aMo_{1-b}M^2{}_bO_x$$

where $M^1$ is Co, Ni, Mg, Zn, Mn and/or Cu; $M^2$ is W, V, Te, Nb, P, Cr, Fe, Sb, Ce, Sn and/or La; a is from 0.5 to 1.5, b is from 0 to 0.5; and x is a number which is determined by the valency and frequency of the elements other than oxygen. These catalysts are disclosed in U.S. Pat. Nos. 6,388,129 B1; 6,423,875 B1; and 6,426,433 B1 as being useful for the conversion of propane to acrolein and/or acrylic acid. These patents are incorporated herein by reference.

The catalyst may comprise an oxidation catalyst represented by the formula $$A_aB_bC_cCa_dFe_eBi_fMo_{12}O_x$$

where A is one or more of Li, Na, K, Rb or Cs; B is one or more of Mg, Sr, Mn, Ni, Co or Zn; C is one or more of Ce, Cr, Al, Sb, P, Ge, Sn, Cu, V or W; a is 0.01 to 1.0; b and e are 1.0 to 10; c is 0 to 5.0, and in one embodiment 0.05 to 5.0, and in one embodiment 0.05 to 4.0; d and f are 0.05 to 5.0; and x is a number determined by the valence requirements of the other elements present. These catalysts are disclosed in U.S. Pat. No. 6,268,529 B1 as being useful for the conversion of propane to acrolein and acrylic acid. This patent is incorporated herein by reference.

The catalyst may comprise an oxidation catalyst represented by the formula $$Mo_{12}V_{4.8}Sr_{0.5}W_{2.4}Cu_{2.2}O_x$$

where x is the quantity of oxygen bonded to the other elements and depends on their oxidation state. This catalyst is disclosed in U.S. Pat. No. 6,310,240 B1 as being useful in the conversion of acrolein to acrylic acid. This patent is incorporated herein by reference.

The catalyst may comprise an oxidation catalyst represented by the formula $$Mo_aW_bV_cA_dB_eO_x$$

wherein A is Fe, Cu, Bi, Cr, Sn, Sb, Ni, Co, Mn, Ce or Tl; B is an alkali or alkaline earth metal; and a, b, c, d, e and x respectively indicate the atomic ratio for Mo, W, V, A, B and O. When a is 10, b is 1.5 to 4, c is 1 to 5, d is 1 to 4, e is 0 to 2, and x is determined according to oxidation states of the other elements. This catalyst is disclosed in U.S. Pat. No. 6,384,275 B2 as being useful for the conversion of acrolein to acrylic acid. This patent is incorporated herein by reference.

The catalyst may comprise an oxidation catalyst represented by the formula $$Mo_{12}V_aX^1{}_bX^2{}_cX^3{}_dX^4{}_eX^5{}_fX^6{}_gO_n$$

where $X^1$ is W, Nb, Ta, Cr and/or Ce; $X^2$ is Cu, Ni, Co, Fe, Mn and/or Zn; $X^3$ is Sb and/or Bi; $X^4$ is one or more alkali metals; $X^5$ is one or more alkaline earth metals; $X^6$ is Si, Al, Ti and/or Zr; a is from 1 to 6; b is from 0.2 to 4; c is from 0.5 to 18; d is from 0 to 40; e is from 0 to 2; f is from 0 to 4; g is from 0 to 40 and n is a number which is determined by the valency and frequency of the elements other than oxygen. This catalyst is disclosed in U.S. Pat. No. 6,403,829 B2 as being useful for the conversion of acrolein to acrylic acid. This patent is incorporated herein by reference.

The catalyst may comprise an oxidation catalyst represented by the formula $$Mo_aV_bW_cCu_dX_eO_g$$

wherein X is at least one element selected from the group consisting of Mg, Ca, Sr and Ba, and a, b, c, d, e, and g are atomic ratios respectively of Mo, V, W, Cu, X and O such that when a is 12, b is in the range of 2 to 14, c in the range of 0 to 12, d in the range of 0 to 6 excluding 0 (0.1 to 6, for example), e is in the range of 0 to 3, and g is a numeral to be determined by the oxidized states of the elements. This catalyst is disclosed in U.S. Pat. No. 6,429,332 B1 as being useful for the conversion of acrolein to acrylic acid. This patent is incorporated herein by reference.

The catalyst may comprise an oxidation catalyst represented by the formula $$Mo_aW_bBi_cFe_dA_eB_fC_gD_hE_iO_x$$

wherein: A is Ni or Co; B is Na, K, Rb, Cs or Tl; C is an alkaline earth metal; D is P, Te, Sb, Sn, Ce, Pb, Nb, Mn, As, B or Zn; and E is Si, Al, Ti or Zr. When a is 12, b is from 0 to 10, c is from 0 to 10, d is from 0 to 10, e is from 2 to 15, f is from 0 to 10, g is from 0 to 10, h is from 0 to 4, i is from 0 to 30, and x is determined by the degree of oxidation of each of the elements. This catalyst is disclosed in U.S. Pat. No. 6,383,973 B1 as being useful for the conversion of propylene, isobutylene, t-butanol or methyl-t-butyl ether to (meth)acrolein or (meth)acrylic acid. This patent is incorporated herein by reference.

The catalyst may comprise an oxidation catalyst represented by the formula $$Mo_aP_bA_cB_dC_eD_fO_x$$

wherein A is at least one element selected from the group consisting of As, Sb, Ge, Bi, Zr, Ce and Se; B is at least one element selected from the group consisting of Cu, Fe, Cr, Ni, Mn, Co, Sn, Ag, Zn, Pd, Rh and Te; C is at least one element selected from the group consisting of V, W and Nb; D is at least one element selected from the group consisting of alkali metals, alkaline earth metals and Tl, and a, b, c, d, e, f, and x are atomic ratios respectively of Mo, P, A, B, C, D, and O such that when a is 12, b is a numeral in the range of 0.5 to 4, and in one embodiment 0.5 to 3; c is in the range of 0 to 5, and in one embodiment 0.01 to 3; d in the range of 0 to 3, and in one embodiment 0.01 to 2; e is in the range or 0 to 4, and in one embodiment 0.01 to 3; f is in the range or 0.01 to 4, and in one embodiment 0.01 to 3, and x is a numeral to be determined by the oxidized states of the elements. This catalyst is disclosed in U.S. Pat. No. 5,618,974 as being useful for the conversion of methacrolein, isobutyl aldehyde, or isobutyric acid to methacrylic acid. This patent is incorporated herein by reference.

The catalyst may comprise an oxidation catalyst containing Mo, V, Nb and Pd, or Mo, La, V and Pd. Specific examples include $$MoV_{0.396}Nb_{0.128}Pd_{0.000384}$$

and $$MoV_{0.628}Pd_{0.000288}La_{0.00001}$$

These catalysts are disclosed in U.S. Pat. No. 6,274,764 B1, which is incorporated herein by reference.

U.S. Pat. No. 6,143,921, which is incorporated herein by reference, discloses three oxidation catalysts, any one of which may be used with the inventive process. The first catalyst is represented by the formula $Mo_aV_bNb_cPd_d$, wherein: a is 1 to 5; b is 0 to 0.5; c is 0.01 to 0.5; and d is 0 to 0.2. The numerical values of a, b, c and d represent the relative gram-atom ratios of the elements Mo, V, Nb and Pd, respectively, in the catalyst. The elements are present in combination with the oxygen in the form of various oxides. The second catalyst has a composition comprising the elements Mo, V, Pd, Nb, La, and X where X is Al, Ga, Si or Ge in the form of oxides in the ratio $Mo_aV_bLa_cPd_dNb_eX_f$ wherein: a is 1; b is 0.01 to 0.9; c is >0 to 0.2; d is >0 to 0.2; e is >0 to 0.2; and f is >0 to 0.3. The third catalyst is formed from a calcined composition represented by the formula $Mo_aV_bNb_cX_d$, wherein X is at least one promoter element selected from the group consisting of: P, B, Hf, Te and As; a is about 1 to 5; b is 1; c is about 0.01 to 0.5; and d is about 0 to 0.1.

The catalyst may be an oxidation catalyst which comprises in combination with oxygen the elements molybdenum, vanadium, niobium and gold according to the formula:

$$Mo_aW_bAu_cV_dNb_eY_f$$

wherein: Y is one or more elements selected from the group consisting of Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te, La and Pd; a, b, c, d, e and f represent the gram atom ratios of the elements such that $1<a\leq 1$; $0<b<1$; $a+b=1$; $10^{-5}\leq c\leq 0.02$; $0<d\leq 2$; $0<e\leq 1$; and $0<f<2$. This catalyst is disclosed in U.S. Pat. No. 6,333,444 B1 as being useful for the oxidation of ethane or ethylene to acetic acid. This patent in incorporated herein by reference.

The catalyst may be an oxidation catalyst having a calcined composition represented by the formula $Mo_aV_bNb_cPd_d$, wherein: 1 is 1 to 5; b is 0 to 0.5; c is 0.01 to 0.5; and d is 0 to 0.2. This catalyst is disclosed in U.S. Pat. No. 6,383,977 B1 for converting ethane to acetic acid. This patent is incorporated herein by reference.

U.S. Pat. No. 6,441,227 B1, which is incorporated herein by reference, discloses two oxidation catalysts which can be used separately or in combination with each other in the inventive process. The first catalyst is a mixed metal oxide represented by formula $$Mo_aPd_bBi_cFe_dX^1_eX^2_fX^3_gO_z$$

wherein: $X^1$ is at least one or more of Co, Ni, V, Pt or Rh; $X^2$ is at least one or more of Al, Ga, Ge, Mn, Nb, Zn, Ag, P, Si or W; $X^3$ is at least one or more of K, Mg, Rb, Ca, Sr, Ba, Na or In; O is oxygen, and a is 1; $0<b\leq 0.3$; $0<c\leq 0.9$; $0<d\leq 0.9$; $0<e\leq 0.9$; $0<f\leq 0.9$; $0<g<0.3$; and z is a number which satisfies the valences of the other elements in the formula. This catalyst is described as being useful for converting olefins to alpha-beta unsaturated aldehydes. The second catalyst is a metal oxide represented by the formula $$Mo_{a1}V_{b1}Al_{c1}X_{d1}Y_{e1}O_{z1}$$

wherein X is W or Mn or both; Y is at least one or more of Pd, Sb, Ca, P, Ga, Ge, Si, Mg, Nb or K; O is oxygen, and $a_1$ is 1; $b_1$ is 0.01 to 0.9; $0<c_1\leq 0.2$; $0<d_1\leq 0.5$; $0<e_1\leq 0.5$; and $z_1$ is a number which satisfies the valences of the other elements in the formula. This catalyst is described as being suitable for converting an alpha-beta unsaturated aldehyde to an alpha-beta unsaturated carboxylic acid.

The catalyst may comprise an ammoxidation catalyst represented by the formula $$A_aK_bCs_cMg_dNi_eFe_fBi_gMo_{12}O_x$$

wherein A is one or more of the elements selected from Co, Mn, Cr, P, Sb, Te, Na, Ce or W, a is a number from 0 to 5; b is a number from 0 to 0.4; c is a number from 0 to 0.4, provided that the sum of b and c is from 0.1 to 0.4; d, e, f, and g are numbers from about 0.2 to 10, and x is a number determined by the valence requirements of the other elements. This catalyst is disclosed in U.S. Pat. No. 5,093,299 as being useful for the conversion of an olefin (e.g., propylene or isobutylene) to the corresponding unsaturated nitrile (e.g., acrylonitrile or methacrylonitrile) by reacting the olefin, ammonia and oxygen in the presence of the foregoing catalyst. This patent is incorporated herein by reference.

The catalyst may comprise an ammoxidation catalyst represented by the formula $$VSb_aM_mN_nO_x$$

where a is 0.5 to 2; M is one or more of Sn, Ti, Fe or Ga; m is 0.05 to 3; N is one or more of: W, Bi, Mo, Li, Mg, P, Zn, Mn, Te, Ge, Nb, Zr, Cr, Al, Cu, Ce or B; n is 0.0 to 0.5; and x is a number determined by the degree of oxidation of each of the other elements. This catalyst is disclosed in U.S. Pat. No. 5,258,543 as being useful for the ammoxidation of $C_3$ to $C_5$ monoolefins to alpha, beta-monounsaturated acyclic nitrites (e.g., acrylonitrile) having 3 to 5 carbon atoms.

U.S. Pat. No. 6,486,091 B1, which is incorporated herein by reference, discloses an ammoxidation catalyst represented by the formula $$Bi_aMo_bV_cSb_dNb_eA_fB_gO_x$$

wherein: A is one or more elements selected from groups VB (e.g., V, Nb, Ta), VIB (e.g., Cr, Mo, W), VIIB (e.g., Mn, Tc, Re) or VIII (e.g., Fe, Co, Ni) of the periodic table; B is at least one alkali promoter selected from groups IA (e.g., Li, Na, K) or IIA (e.g., Mg, Ca) of the periodic table; a is 0.01 to 12; b is 0.01 to 12; c is 0.01 to 2; d is 0.01 to 10; e is 0.01 to 1; f is 0 to 2; g is 0 to 1; and x is the number of oxygen atoms required to satisfy the valency requirements of the elements present. This catalyst is described as being useful for converting olefins to unsaturated nitriles.

In one embodiment, the catalyst is other than a vanadium phosphorus oxide based catalyst. In one embodiment the catalyst is other than a catalyst represented by the formula $V_2O_5/P_2O_5/TiO_2$.

The catalyst may have any size and geometric configuration that fits within the process microchannels 104. The catalyst may be in the form of particulate solids (e.g., pellets, powder, fibers, and the like) having a median particle diameter of about 1 to about 1000 μm, and in one embodiment about 10 to about 500 μm, and in one embodiment about 25 to about 250 μm. The catalyst may be comprised of a porous structure such as a foam, felt, wad or a combination thereof. The term "foam" is used herein to refer to a structure with continuous walls defining pores throughout the structure. The term "felt" is used herein to refer to a structure of fibers with interstitial spaces therebetween. The term "wad" is used herein to refer to a structure of tangled strands, like steel wool. The catalyst may have a honeycomb structure, or the structure of an insertable fin. The fin may have straight channels or may take the form of an offset strip fin. The number of fins per inch may range from about 4 to about 90. The fins may have a thickness of about 0.02 to about 2.5 mm.

Figures 5, 6:
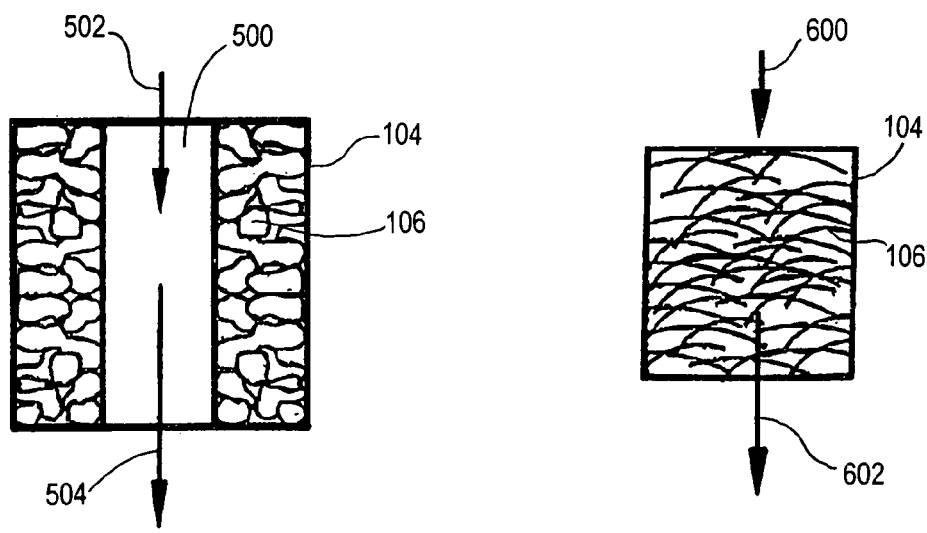
FIG. 5 is a schematic illustration of a cross-sectional view of a process microchannel used with the inventive process, the process microchannel containing a catalyst having a flow-by configuration.
FIG. 6 is a cross-sectional view of an alternate embodiment of the process microchannel used with the inventive process, the process microchannel containing a catalyst having a flow-through configuration.

The catalyst may be in the form of a flow-by structure such as a felt with an adjacent gap, a foam with an adjacent gap, a fin structure with gaps, a washcoat on any inserted substrate, or a gauze that is parallel to the flow direction with a corresponding gap for flow. An example of a flow-by structure is illustrated in FIG. 5. In FIG. 5, the catalyst 106 is contained within process microchannel 104. An open passage way 500 permits the flow of fluid through the process microchannel 104 in contact with the catalyst 106 as indicated by arrows 502 and 504.

The catalyst may be in the form of a flow-through structure such as a foam, wad, pellet or powder, or gauze. An example of a flow-through structure is illustrated in FIG. 6. In FIG. 6, the flow-through catalyst 106 is contained within process microchannel 104 and the fluid flows through the catalyst 106 as indicated by arrows 600 and 602.

The catalyst may be directly washcoated on the interior walls of the process microchannels, grown on the walls from solution, or coated in situ on a fin structure. The catalyst may be in the form of a single piece of porous contiguous material, or many pieces in physical contact. In one embodiment, the catalyst is comprised of a contiguous material and has a contiguous porosity such that molecules can diffuse through the catalyst. In this embodiment, the fluids flow through the catalyst rather than around it. In one embodiment, the cross-sectional area of the catalyst occupies about 1 to about 99%, and in one embodiment about 10 to about 95% of the cross-sectional area of the process microchannels. The catalyst may have a surface area, as measured by BET, of greater than about 0.5 m$^2$/g, and in one embodiment greater than about 2 m$^2$/g.

The catalyst may comprise a porous support, an interfacial layer on the porous support, and a catalyst material on the interfacial layer. The interfacial layer may be solution deposited on the support or it may be deposited by chemical vapor deposition or physical vapor deposition. In one embodiment the catalyst has a porous support, a buffer layer, an interfacial layer, and a catalyst material. Any of the foregoing layers may be continuous or discontinuous as in the form of spots or dots, or in the form of a layer with gaps or holes.

The catalyst may be supported on a porous substrate having a porosity of at least about 5% as measured by mercury porosimetry and an average pore size (sum of pore diameters divided by number of pores) of about 1 to about 1000 μm. The porous support may be a porous ceramic or a metal foam. Other porous supports that may be used include carbides, nitrides, and composite materials. The porous support may have a porosity of about 30% to about 99%, and in one embodiment about 60% to about 98%. The porous support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the support and the interfacial layers, and in one embodiment has a coefficient of thermal expansion that is intermediate the thermal expansion coefficients of the porous support and the interfacial layer. The buffer layer may be a metal oxide or metal carbide. The buffer layer may be comprised of $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. $\alpha$-$Al_2O_3$ provides the advantage of excellent resistance to oxygen diffusion. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer.

The porous support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 μm, and in one embodiment about 0.05 to about 5 μm.

In one embodiment of the invention, adequate adhesion and chemical stability may be obtained without a buffer layer. In this embodiment the buffer layer may be omitted.

The interfacial layer may be comprised of nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may be comprised of a metal oxide. Examples of metal oxides that may be used include $\gamma$-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. Usually, however, the interfacial layer is used in combination with a catalytically active layer. The interfacial layer may also be formed of two or more compositionally different sublayers. The interfacial layer may have a thickness that is less than one half of the average pore size of the porous support. The interfacial layer thickness may range from about 0.5 to about 100 µm, and in one embodiment from about 1 to about 50 µm. The interfacial layer may be either crystalline or amorphous. The interfacial layer may have a BET surface area of at least about 1 m$^2$/g.

The catalyst may comprise any of the catalyst materials discussed above deposited on the interfacial layer. Alternatively, the catalyst material may be simultaneously deposited with the interfacial layer. The catalyst layer may be intimately dispersed on the interfacial layer. That the catalyst layer is "disposed on" or "deposited on" the interfacial layer includes the conventional understanding that microscopic catalyst particles are dispersed: on the support layer (i. e., interfacial layer) surface, in crevices in the support layer, and in open pores in the support layer.

The contact time of the reactants and/or products with the catalyst 106 within the process microchannels 104 may range from about 0.1 ms to about 100 seconds, and in one embodiment about 0.1 ms to about 20 seconds, and in one embodiment about 0.1 ms to about 10 seconds, and in one embodiment about 0.1 ms to about 5 seconds, and in one embodiment about 0.1 ms to about 1 second, and in one embodiment from about 1 ms to about 750 ms, and in one embodiment about 5 ms to about 750 ms, and in one embodiment about 10 to about 500 ms, and in one embodiment about 10 to about 250 ms.

The space velocity (or gas hourly space velocity) for the flow of the reactant composition and product through the process microchannels may be at least about 100 hr$^{-1}$ (normal liters of hydrocarbon/hour/liter of reaction chamber) or at least about 100 ml feed/(g catalyst) (hr). The space velocity may range from about 100 to about 2,000,000 hr$^{-1}$ based on the volume of the process microchannels, or from about 100 to about 2,000,000 ml feed/(g catalyst) (hr). In one embodiment, the space velocity may range from about 500 to about 1,000,000 hr$^{-1}$, or about 500 to about 1,000,000 ml feed/(g catalyst) (hr), and in one embodiment from about 1000 to about 1,000,000 hr$^{-1}$, or from about 1000 to about 1,000,000 ml feed/(g catalyst) (hr).

The temperature of the reactant composition entering the process microchannels 104 may range from about 150° C. to about 1000° C., and in one embodiment about 150° C. to about 700° C., and in one embodiment about 150° C. to about 600° C., and in one embodiment about 200° C. to about 600° C. In one embodiment the temperature may be in the range of about 150° C. to about 500° C., and in one embodiment about 150° C. to about 400° C., and in one embodiment about 200° C. to about 300° C. In one embodiment, the temperature may be in the range of about 335° C. to about 1000° C.

The reactant composition entering the process microchannels 104 may be at a pressure of at least about 0.5 atmosphere, and in one embodiment at least about 0.9 atmosphere. In one embodiment the pressure may range from about 0.5 to about 100 atmospheres, and in one embodiment from about 0.9 to about 50 atmospheres, and in one embodiment about 0.9 to about 40 atmospheres, and in one embodiment from about 0.9 to about 35 atmospheres.

The pressure drop of the reactants and/or products as they flow through the process microchannels 104 may range up to about 30 pounds per square inch per foot of length of the process microchannel (psi/ft), and in one embodiment up to about 15 psi/ft, and in one embodiment up to 5 psi/ft, and in one embodiment up to about 2 psi/ft.

The flow of the reactants and/or products through the process microchannels may be laminar or in transition, and in one embodiment it is laminar. The Reynolds Number for the flow of reactants and/or products through the process microchannels may be up to about 4000, and in one embodiment up to about 2300, and in one embodiment in the range of about 10 to about 2000, and in one embodiment about 100 to about 1500.

The heat exchange fluid entering the heat exchange channels may have a temperature of about −70° C. to about 650° C., and in one embodiment about 0° C. to about 500° C., and in one embodiment about 100° C. to about 300° C. The heat exchange fluid exiting the heat exchange channels may have a temperature in the range of about −60° C. to about 630° C., and in one embodiment about 10° C. to about 490° C. The residence time of the heat exchange fluid in the heat exchange channels may range from about 1 to about 1000 ms, and in one embodiment about 1 to about 500 ms, and in one embodiment from 1 to about 100 ms. The pressure drop for the heat exchange fluid as it flows through the heat exchange channels may range from about 0.05 to about 50 psi/ft, and in one embodiment from about 1 to about 25 psi/ft. The flow of the heat exchange fluid through the heat exchange channels may be laminar or in transition, and in one embodiment it is laminar. The Reynolds Number for the flow of heat exchange fluid flowing through the heat exchange channels may be up to about 4000, and in one embodiment up to about 2300, and in one embodiment in the range of about 10 to about 2000, and in one embodiment about 10 to about 1500.

The product exiting the microchannel reactor may be at a temperature in the range of about 100° C. to about 1000° C., and in one embodiment about 200° C. to about 800° C., and in one embodiment about 300° C. to about 600° C.; and during step (C) it may be cooled to a temperature in the range of about 50° C. to about 300° C., and in one embodiment about 50° C. to about 200° C., and in one embodiment about 50° C. to about 150° C., and in one embodiment about 50° C. to about 100° C., in about 5 to about 100 ms, and in one embodiment about 5 to about 75 ms, and in one embodiment about 5 to about 50 ms, and in one embodiment about 10 to about 50 ms.

The product formed by the inventive process may comprise an oxygenate or a nitrile. The oxygenates include alcohols, epoxides, aldehydes, carboxylic acids, carboxylic acid anhydrides, esters, and the like. The oxygenates include, with the exception of the epoxides and esters, one or more of the above-indicated oxygenates containing 1 to about 20 carbon atoms per molecule, and in one embodiment 1 to about 18 carbon atoms, and in one embodiment 1 to about 16 carbon atoms, and in one embodiment 1 to about 14 carbon atoms, and in one embodiment 1 to about 12 carbon atoms, and in one embodiment 1 to about 10 carbon atoms, and in one embodiment about 2 to about 6 carbon atoms, and in one embodiment about 2 to about 4 carbon atoms per molecule. The epoxides and esters must contain at least 2 carbon atoms, but in all other respects would include compounds within the above-indicated ranges, for example, 2 to about 20 carbon atoms, etc. The alcohols include monools and polyols. Specific examples include methanol, ethyl alcohol, propyl alcohol, butyl alcohol, isobutyl alcohol, pentyl alcohol, cyclopentyl alcohol, crotyl alcohol, hexyl alcohol, cyclohexyl alcohol, allyl alcohol, benzyl alcohol, glycerol, and the like. The epoxides include ethylene oxide, propylene oxide, butylene oxide, isobutylene oxide, cyclopentene oxide, cyclohexene oxide, styrene oxide, and the like. The aldehydes include formaldehyde; acetaldehyde; propionaldehyde; n-butyraldehyde; n-valeraldehyde; caproaldehyde; acrolein; tran-2-cis-6-nonadienal; n-heptylaldehyde; trans-2-hexenal; hexadeconal; benzaldehyde; phenylacetaldehyde; o-tolualdehyde; m-tolualdehyde; p-tolualdehyde; salicylaldehyde; p-hydroxybenzaldehyde; and the like. The carboxylic acids include formic acid, acetic acid, propionic acid, butyric acid, isobutyric acid, valeric acid, caproic acid, caprylic acid, capric acid, acrylic acid, methacrylic acid, benzoic acid, toluic acid, phthalic acid, salicylic acid, and the like. The carboxylic acid anhydrides include acetic anhydride, maleic anhydride, phthalic anhydride, benzoic anhydride, and the like. The esters include methyl acetate, vinyl acetate, ethyl acetate, n-propyl acetate, n-butyl acetate, n-pentyl acetate, isopentyl acetate, benzyl acetate, phenyl acetate, and the like.

The nitriles include those containing 1 to about 20 carbon atoms, and in one embodiment 1 to about 18 carbon atoms, and in one embodiment 1 to about 16 carbon atoms, and in one embodiment 1 to about 14 carbon atoms, and in one embodiment 1 to about 12 carbon atoms, and in one embodiment 1 to about 10 carbon atoms, and in one embodiment 1 to about 8 carbon atoms, and in one embodiment 2 to about 6 carbon atoms, and in one embodiment 3 or 4 carbon atoms per molecule. These nitrites include unsaturated nitrites. Specific examples include formonitrile, acrylonitrile, methacrylonitrile, and the like.

In one embodiment, the hydrocarbon reactant used in the reactant composition comprises methane, and the product comprises methanol, formaldehyde, formonitrile, or a mixture thereof.

In one embodiment, the hydrocarbon reactant used in the reactant composition comprises ethane, and the product comprises ethyl alcohol, ethylene oxide, acetic acid, vinyl acetate, or a mixture of two or more thereof.

In one embodiment, the hydrocarbon reactant used in the reactant composition comprises ethylene, and the product comprises ethyl alcohol, ethylene oxide, acetic acid, vinyl acetate, or a mixture of two or more thereof.

In one embodiment, the hydrocarbon reactant used in the reactant composition comprises propane, and the product comprises propylene oxide, acrylic acid, acrolein, acrylonitrile, or a mixture thereof.

In one embodiment, the hydrocarbon reactant used in the reactant composition comprises propylene, and the product comprises propylene oxide, acrylic acid, acrolein, acrylonitrile, or a mixture thereof.

In one embodiment, the hydrocarbon reactant used in the reactant composition comprises n-butane, and the product comprises n-butanol, maleic anhydride, or a mixture of two or more thereof.

In one embodiment, the hydrocarbon reactant used in the reactant composition comprises n-butene, and the product comprises n-butanol, maleic anhydride, or a mixture thereof.

In one embodiment, the hydrocarbon reactant used in the reactant composition comprises isobutane, and the product comprises isobutanol, methacrylic acid, methacrylonitrile, or a mixture thereof.

In one embodiment, the hydrocarbon reactant used in the reactant composition comprises isobutylene, and the product comprises isobutanol, methacrylic acid, methacrylonitrile, or a mixture thereof.

In one embodiment, the hydrocarbon reactant used in the reactant composition comprises cyclopentene, and the product comprises cyclopentene oxide.

In one embodiment, the hydrocarbon reactant used in the reactant composition comprises cyclohexene, and the product comprises cyclohexene oxide.

In one embodiment, the hydrocarbon reactant used in the reactant composition comprises styrene, and the product comprises styrene oxide.

In one embodiment, the hydrocarbon reactant used in the reactant composition comprises toluene, and the product comprises benzyl alcohol, benzaldehyde, benzoic acid, or a mixture thereof.

In one embodiment, the hydrocarbon reactant used in the reactant composition comprises xylene, and the product comprises toluic acid, phthalic acid, phthalic anhydride, or a mixture thereof.

In one embodiment, the hydrocarbon reactant used in the reactant composition comprises acrolein and the product comprises acrylic acid.

Advantages of the inventive process include: maximization of contact between the hydrocarbon reactant, oxygen or source of oxygen, and optionally ammonia, and the catalyst; and minimization of homogenous gas-phase unselective reactions, such as those which convert hydrocarbon reactants or oxygenate or nitrile products to carbon oxides (CO and $CO_2$). In one embodiment, selectivity to carbon oxides (on a carbon atom basis) is less than about 60%, and in one embodiment less than about 40%, and in one embodiment less than about 20%, and in one embodiment less than about 10%, and in one embodiment less than about 5%.

Advantages of the inventive process include the possibility of process intensification. Conventional processes of the prior art often operate under conditions of reactant dilution to prevent runaway reactions, while the inventive process may be operated, if desired, under more intensive conditions leading to greater throughput. By combining catalytic microchannel processing with heat exchange it is possible to operate at hydrocarbon feed/oxygen ratios that would conventionally lead to high temperatures and loss of selectivity, but by removing heat rapidly through heat exchange, the temperature in the process microchannels may be maintained relatively low, for example, below about 700° C., and in one embodiment below about 600° C., and in one embodiment below about 500° C., thus maximizing selectivity to desired products.

Advantages of the inventive process include the enhancement of reaction selectivity due to the dimensions of the microchannel reactor. In reactors of conventional dimension, reactions propagated homogeneously in the in the gaseous phase make a significant contribution to the overall make-up of the product. These reactions tend to be indiscriminate and often result in the production of undesirable by-products such as CO and $CO_2$ or hydrocarbon pyrolysis products. For example, if the reactant mixture contains propane, full and partial oxidation can take place as well as pyrolysis leading to the production of ethane and methane. Significant increases in reaction selectivity to the oxygenate or nitrile product can be achieved when conducted in a microchannel reactor in accordance with the invention wherein the microchannel reactor has an internal height or width at or near the quench diameter for the reaction in question.

The level of conversion of the hydrocarbon reactant may be about 10% or higher, and in one embodiment about 50% or higher, and in one embodiment about 75% or higher, and in one embodiment about 90% or higher.

The level of selectivity of the desired product may be about 40% or higher, and in one embodiment about 50% or higher, and in one embodiment about 60% or higher, and in one embodiment about 70% or higher, and in one embodiment about 80% or higher, and in one embodiment about 85% or higher, and in one embodiment about 90% or higher, and in one embodiment about 95% or higher. In one embodiment, the level of selectivity to the desired product may be in the range of about 50% to about 95%, and in one embodiment about 75% to about 95%.

The yield of the desired product may be about 40% or higher per cycle, and in one embodiment about 50% or higher, and in one embodiment about 60% or higher, and in one embodiment about 70% or higher per cycle, and in one embodiment about 80% or higher, and in one embodiment 85% or higher, and in one embodiment about 90% or higher per cycle. The term "cycle" is used herein to refer to a single pass of the reactants through the process microchannels.

In one embodiment, the level of conversion of the hydrocarbon reactant is at least about 95%, the level of selectivity of the desired product is at least about 95%, and the yield of the desired product is at least about 90% per cycle.

In one embodiment, the process is conducted in a reactor containing a plurality of heat exchange channels operating in parallel, the total pressure drop for the heat exchange fluid flowing through the heat exchange channels is up to about 10 atmospheres, and in one embodiment up to about 5 atmospheres, and in one embodiment up to about 2 atmospheres.

In one embodiment, the thermal efficiency of the heat exchange used in the microchannel reactor is sufficient for the temperature of the exiting product stream (e.g., product stream 130 in FIG. 1 or product stream 320 in FIG. 3A) to be within about 100° C. of the temperature of the entering reactant stream and/or oxidant stream (e.g., reactant stream 120 and/or oxidant stream 122 in FIG. 1, or reactant stream 316 and/or oxidant stream 318 in FIG. 3A), and in one embodiment within about 75° C., and in one embodiment within about 50° C., and in one embodiment within about 25° C., and in one embodiment within about 10° C.

Unlike conventional reaction vessels for oxidations and ammoxidations which have to take into account the possibility of explosions for mixtures of oxygen and hydrocarbon, the possibility of such explosions with the inventive process is of less concern. This is believed to be due to the relatively brief catalyst contact times employed in the process microchannels, the added cooling provided by Step (B) of the process, and the dimensions of the microchannels which make them effective flame arresters preventing the propagation of combustion reactions and flames that would normally lead to explosions and/or detonations. Thus, with the inventive process it is permissible to operate at least partly in the explosion range without incurring an explosion.

EXAMPLES 1-8

In the following Examples 1-8, the reaction process illustrated in FIGS. 3A and 3B is used. The microchannel reactor 300 is fabricated from six distinct pieces: microchannel reactor core 301, reactant header 302, oxidant header 304, product footer 306, heat exchange header 310 and heat exchange footer 312. Each piece is fabricated from 316 stainless steel. Alternatively, other steel alloys, Inconel 617 or other nickel alloys, FeCrAlY or other high temperature alloys could be used. The reactant header, oxidant header and product footer have a common design and construction. The heat exchange header and heat exchange footer have a common design and construction. The headers and footers are formed by machining a pocket in a solid block using an end mill. Alternatively, the headers and footers could be fabricated via welding from standard pipe, or any method that is suitable to the material of construction and overall size of the device including stacking and bonding laminate sheets.

The microchannel reactor core 301 is fabricated using microcomponent sheet architecture. The microchannel reactor core 301 contains two zones, reactor zone 307, and manifold and recuperator zone 308. These zones are differentiated primarily by the fact that in the reactor zone 307 heat exchange microchannels 380 and 390 run in alternating planes to the oxidant microchannels 360 and process microchannels 340 and 350. The catalyst is present in the process microchannels 340 and 350 in the reaction zone 307 in the form of a packed bed of powder. Alternatively, the catalyst could be in the form of a foam, felt, wad or washcoated insert. The catalyst could be directly washcoated on the interior walls of the process microchannels 340 and 350.

The microchannel core reactor 301 is assembled by joining together all of the microcompent sheets via diffusion bonding. Alternatively, the sheets could be joined via diffusion brazing, brazing, laser welding or other suitable techniques. The reactant header 302, oxidant header 304, product footer 306 and heat exchange header 310 and heat exchange footer 312 are attached to the microchannel core reactor 301 by welding or brazing. Alternatively, the reactant header, oxidant header, product footer and the heat exchange header and footer may be attached to the microchannel core reactor during the joining step.

The reactant composition comprising the hydrocarbon reactant, and optionally ammonia, flows into the microchannel reactor 300 through the reactant header 302, as indicated by directional arrow 316. The oxygen or source of oxygen flows into the microchannel reactor 300 through the oxidant header 304 as indicated by directional arrow 318. The hydrocarbon reactant, oxygen or source of oxygen, and optionally ammonia, flow into and through the manifold and recuperator 308 into the reactor zone 307 wherein they contact the catalyst and react to form the desired product. The product flows from the reactor zone 307 through an internal manifold to recuperator 308, where product quench may occur, then to product footer 306, and from product footer 306, optionally through quenching apparatus 314, as indicated by directional arrows 320 and 322. A heat exchange fluid flows into heat exchange header 310, as indicated by directional arrow 324, and then from heat exchange header 310 through microchannel reactor core 301 to heat exchange footer 312, and then out of heat exchange footer 312, as indicated by directional arrow 326. Within the microchannel reactor core 301, the oxygen or source of oxygen is added to the hydrocarbon reactant, and optionally ammonia, using staged addition as illustrated in FIG. 3B and discussed above.

EXAMPLE 1

The hydrocarbon reactant is ethylene. The source of oxygen is air. The oxygen is mixed with the ethylene using staged addition, the volumetric ratio of air to ethylene when fully mixed being 86:14. The catalyst is an oxidation catalyst. The heat exchange fluid is Dowtherm A. The heat exchange fluid undergoes partial boiling in the heat exchange microchannels 380 and 390. The ethylene and air are preheated to a temperature of 100° C. The ethylene flows through header 302 into the reaction zones 342 and 352 of the process microchannels 340 and 350, respectively. The air flows through header 304 into oxidant microchannel 360. The air flows through oxidant microchannel 360 into orifices 370, and through orifices 370 into the reaction zones 342 and 352 where it mixes with the ethylene. The ethylene and air contact the catalyst and undergo reaction to form a product comprising acetic acid. The catalyst contact time is 50 ms. The product exits the reaction zones 342 and 352 at a temperature of 285° C. The product is quenched to a temperature of 125° C. in 50 milliseconds in recuperator 308.

EXAMPLE 2

The reactant composition contains a mixture of ethylene, acetic acid, water and nitrogen at a volumetric ratio of 50:20:1:21. The source of oxygen is oxygen. The oxygen is mixed with the reactant composition using staged addition, the volumetric ratio of the reactant composition to the oxygen when fully mixed being 92:8. The catalyst is an oxidation catalyst. The heat exchange fluid is Dowtherm A. The heat exchange fluid undergoes partial boiling in the heat exchange microchannels 380 and 390. The reactant composition and oxygen are preheated to a temperature of 100° C. The reactant composition flows through header 302 into the reaction zones 342 and 352 of the process microchannels 340 and 350, respectively. The oxygen flows through header 304 into oxidant microchannel 360. The oxygen flows through oxidant microchannel 360 into orifices 370, and through orifices 370 into the reaction zones 342 and 352 where it mixes with the reactant composition. The reactant composition and oxygen contact the catalyst and undergo reaction to form a product comprising vinyl acetate. The catalyst contact time is 50 ms. The product exits the reaction zones 342 and 352 at a temperature of 160° C. The product is quenched to a temperature of 110° C. in 50 milliseconds in recuperator 308.

EXAMPLE 3

The hydrocarbon reactant is propylene. The source of oxygen is air. The air is mixed with the propylene using staged addition, the volumetric ratio of air to propylene when fully mixed being 94:6. The catalyst is an oxidation catalyst. The heat exchange fluid is Dowtherm A. The propylene and air are preheated to a temperature of 200° C. The propylene flows through header 302 into the reaction zones 342 and 352 of the process microchannels 340 and 350, respectively. The air flows through header 304 into oxidant microchannel 360. The air flows through oxidant microchannel 360 into orifices 370, and through orifices 370 into the reaction zones 342 and 352 where it mixes with the propylene. The propylene and air contact the catalyst and undergo reaction to form a product comprising acrolein. The catalyst contact time is 50 ms. The product exits the reaction zones 342 and 352 at a temperature of 360° C. The product is quenched to a temperature of 210° C. in recuperator 308. The product is then quenched to a temperature of 100° C. in 50 milliseconds in quenching apparatus 314.

EXAMPLE 4

The reactant composition contains of acrolein and steam at a volumetric ratio of 6:10. The source of oxygen is air. The air is mixed with the reactant composition using staged addition, the volumetric ratio of air to the reactant composition when fully mixed being 84:16. The catalyst is an oxidation catalyst. The heat exchange fluid is Dowtherm A. The reactant composition and air are preheated to a temperature of 100° C. The reactant composition flows through header 302 into the reaction zones 342 and 352 of the process microchannels 340 and 350, respectively. The air flows through header 304 into oxidant microchannel 360. The air flows through oxidant microchannel 360 into orifices 370, and through orifices 370 into the reaction zones 342 and 352 where it mixes with the reactant composition. The reactant composition and air contact the catalyst and undergo reaction to form a product comprising acrylic acid. The catalyst contact time is 50 ms. The product exits the reaction zones 342 and 352 at a temperature of 275° C. The product is quenched to a temperature of 50° C. in 50 milliseconds in recuperator 308.

EXAMPLE 5

The reactant composition contains propane and steam at a volumetric ratio of 25:65. The source of oxygen is oxygen. The oxygen is mixed with the reactant composition using staged addition, the volumetric ratio of oxygen to the reactant composition when fully mixed being 10:90. The catalyst is an oxidation catalyst. The heat exchange fluid is steam. The reactant composition and oxygen are preheated to a temperature of 200° C. The reactant composition flows through header 302 into the reaction zones 342 and 352 of the process microchannels 340 and 350, respectively. The oxygen flows through header 304 into oxidant microchannel 360. The oxygen flows through oxidant microchannel 360 into orifices 370, and through orifices 370 into the reaction zones 342 and 352 where it mixes with the reactant composition. The reactant composition and oxygen contact the catalyst and undergo reaction to form a product comprising acrylic acid. The catalyst contact time is 50 ms. The product exits the reaction zones 342 and 352 at a temperature of 400° C. The product is quenched to a temperature of 210° C. in 50 milliseconds in recuperator 308. The product is quenched to a temperature of 50° C. in 50 milliseconds in quenching apparatus 314.

EXAMPLE 6

The reactant composition contains propene, nitrogen and steam at a volumetric ratio of 6.7:62:20. The source of oxygen is oxygen. The oxygen is mixed with the reactant composition using staged addition, the volumetric ratio of oxygen to the reactant composition when fully mixed being 11.3:88.7. The catalyst is an oxidation catalyst. The heat exchange fluid is Dowtherm A. The reactant composition and oxygen are preheated to a temperature of 200° C. The reactant composition flows through header 302 into the reaction zones 342 and 352 of the process microchannels 340 and 350, respectively. The oxygen flows through header 304 into oxidant microchannel 360. The oxygen flows through oxidant 30 microchannel 360 into orifices 370, and through orifices 370 into the reaction zones 342 and 352 where it mixes with the reactant composition. The reactant composition and oxygen contact the catalyst and undergo reaction to form a product comprising acrylic acid. The catalyst contact time is 50 ms. The product exits the reaction zones 342 and 352 at a temperature of 360° C. The product is quenched to a temperature of 225° C. in recuperator 308. The product is then quenched to a temperature of 50° C. in 50 milliseconds in quenching apparatus 314.

EXAMPLE 7

The hydrocarbon reactant is xylene. The source of oxygen is oxygen. The oxygen is mixed with the xylene using staged addition, the volumetric ratio of oxygen to the xylene when fully mixed being 99:1. The catalyst is an oxidation catalyst. The heat exchange fluid is steam. The xylene and oxygen are preheated to a temperature of 120° C. The xylene flows through header 302 into the reaction zones 342 and 352 of the process microchannels 340 and 350, respectively. The oxygen flows through header 304 into oxidant microchannel 360. The oxygen flows through oxidant microchannel 360 into orifices 370, and through orifices 370 into the reaction zones 342 and 352 where it mixes with the xylene. The xylene and oxygen contact the catalyst and undergo reaction to form a product comprising phthalic anhydride. The catalyst contact time is 50 ms. The product exits the reaction zones 342 and 352 at a temperature of 450° C. The product is then quenched to a temperature of 175° C. in 50 milliseconds in recuperator 308. The product is quenched to a temperature of 50° C. in 50 milliseconds in quenching apparatus 114.

EXAMPLE 8

The reactant composition contains propane and ammonia at a volumetric ratio of 6:7. The source of oxygen is air. The air is mixed with the reactant composition using staged addition, the volumetric ratio of air to the reactant composition when fully mixed being 87:13. The catalyst is an ammoxidation catalyst. The heat exchange fluid is steam. The reactant composition and oxygen are preheated to a temperature of 150° C. The reactant composition flows through header 302 into the reaction zones 342 and 352 of the process microchannels 340 and 350, respectively. The air flows through header 304 into oxidant microchannel 360. The air flows through oxidant microchannel 360 into orifices 370, and through orifices 370 into the reaction zones 342 and 352 where it mixes with the reactant composition. The reactant composition and air contact the catalyst and undergo a reaction to form a product comprising acrylonitrile. The catalyst contact time is 50 ms. The product exits the reaction zones 342 and 352 at a temperature of 460° C. The product is quenched to a temperature of 160° C. in 50 milliseconds in recuperator 308.

EXAMPLES 9-12

In the following Examples 9-12, the reaction process illustrated in FIG. 2 is used. In these examples, the hydrocarbon reactant, and oxygen or source of oxygen, and optionally ammonia, are premixed and preheated prior to entering the process microchannels. Upon entering the process microchannels, the reactants contact a catalyst and undergo an exothermic reaction to form a desired product. The process microchannels are subjected to cooling during this reaction using an adjacent heat exchanger. The product is then quenched. The process microchannels have a reaction zone containing the catalyst, and a channel zone downstream of the catalyst wherein the product is subjected to cooling prior to exiting the process microchannels.

EXAMPLE 9

The hydrocarbon reactant is ethane. The source of oxygen is oxygen. The oxygen is mixed with the ethane, the volumetric ratio of oxygen to ethane being 18:82. The catalyst is an oxidation catalyst. The heat exchange fluid is air. The ethane and oxygen are preheated to a temperature of 200° C. and then flow into the process microchannels where they contact the catalyst and undergo an exothermic reaction to form a product comprising acetic acid. The catalyst contact time is 50 ms. The product exits the reaction zone within the process microchannels at a temperature of 260° C., and exits channel zone within the process microchannels at a temperature of 210° C. The product is quenched to a temperature of 50° C. in 50 milliseconds in quenching apparatus 136.

EXAMPLE 10

The hydrocarbon reactant is propane. The source of oxygen is air. The air is mixed with the propane, the volumetric ratio of air to propane being 20:80. The catalyst is an oxidation catalyst. The heat exchange fluid is steam. The propane and air are preheated to a temperature of 200° C. and then flow into the process microchannels where they contact the catalyst and undergo an exothermic reaction to form a product comprising acrolein. The catalyst contact time is 25 ms. The product exits the reaction zone within the process microchannels at a temperature of 480° C., and exits the channel zone within the process microchannels at a temperature of 220° C. The product is quenched to a temperature of 100° C. in 50 milliseconds in quenching apparatus 136.

EXAMPLE 11

The reactant composition contains a mixture of n-butane and water at a volumetric ratio of 1:1. The source of oxygen is air. The air is mixed with the reactant composition, the volumetric ratio of air to the reactant composition being 98:2. The catalyst is an oxidation catalyst. The heat exchange fluid is steam. The reactant composition and air are preheated to a temperature of 2000° C. and then flow into the process microchannels where they contact the catalyst and undergo an exothermic reaction to form a product comprising maleic anhydride. The catalyst contact time is 50 ms. The product exits the reaction zone within the process microchannels at a temperature of 460° C., and exits the channel zone within the process microchannels at a temperature of 220° C. The product is quenched to a temperature of 150° C. in 50 milliseconds in quenching apparatus 136.

EXAMPLE 12

The reactant composition contains a mixture of propylene and ammonia at a volumetric ratio of 8.5:10.5. The source of oxygen is air. The air is mixed with the reactant composition, the volumetric ratio of air to the reactant composition being 81:19. The catalyst is an ammoxidation catalyst. The heat exchange fluid is steam. The reactant composition and air are preheated to a temperature of 200° C. and then flow into the process microchannels where they contact the catalyst and undergo an exothermic reaction to form a product comprising acrylonitrile. The catalyst contact time is 50 ms. The product exits the reaction zone within the process microchannels at a temperature of 440° C., and exits the channel zone within the process microchannels at a temperature of 220° C. The product is quenched to a temperature of 150° C. in 50 milliseconds in quenching apparatus 136.

While the invention has been explained in relation to various detailed embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process for converting a hydrocarbon reactant to a product, the process comprising:
   (A) flowing a reactant composition comprising the hydrocarbon reactant, and oxygen or a source of oxygen, and optionally ammonia, in a microchannel reactor in contact with a catalyst to convert the hydrocarbon reactant to the product, the product comprising an oxygenate or a nitrile, the oxygen or source of oxygen being added to the hydrocarbon reactant, and optionally ammonia, using staged addition wherein oxygen or a source of oxygen is added to the hydrocarbon reactant, and optionally ammonia, at various points in the microchannel reactor, the hydrocarbon reactant undergoing an exothermic reaction in the microchannel reactor;
   (B) transferring heat from the microchannel reactor to a heat exchanger during step (A); and
   (C) quenching the product from step (A).

2. The process of claim 1 wherein the microchannel reactor comprises at least one process microchannel containing the catalyst, and the heat exchanger is adjacent to the process microchannel.

3. The process of claim 1 wherein the microchannel reactor comprises a plurality of process microchannels containing the catalyst, the reactant composition entering the process microchannels and the product exiting the process microchannels, the temperature of the reactant composition entering the process microchannels being within about 200° C. of the temperature of the product exiting the process microchannels.

4. The process of claim 1 wherein the reactant composition is preheated prior to step (A).

5. The process of claim 1 wherein the reactant composition and oxygen or oxygen source are mixed prior to step (A).

6. The process of claim 1 wherein the reactant composition and oxygen or oxygen source are mixed during step (A).

7. The process of claim 1 wherein the microchannel reactor comprises a plurality of process microchannels containing the catalyst, a header providing a flow passageway for fluid to enter the process microchannels, and a footer providing a flow passageway for fluid to leave the process microchannels.

8. The process of claim 7 wherein each process microchannel has an internal dimension of width or height of up to about 10 mm.

9. The process of claim 7 wherein each of the process microchannels has an entrance, an exit and an elongated section extending between the entrance and the exit, the process microchannels further comprising at least one additional entrance in the elongated section, the oxygen or source of oxygen entering the process microchannels through the at least one additional entrance.

10. The process of claim 7 wherein the process microchannels are made of a material comprising: steel; monel; inconel; aluminum; titanium; nickel; copper; brass; an alloy of any of the foregoing metals; a polymer; ceramics; glass; a composite comprising a polymer and fiberglass; quartz; silicon; or a combination of two or more thereof.

11. The process of claim 7 wherein the heat exchanger comprises heat exchange channels in thermal contact with the process microchannels.

12. The process of claim 11 wherein the heat exchange channels comprise microchannels.

13. The process of claim 12 wherein each heat exchange microchannel has an internal dimension of width or height of up to about 10 mm.

14. The process of claim 11 wherein the heat exchange channels are made of a material comprising: steel; monel; inconel; aluminum; titanium; nickel; copper; brass; an alloy of any of the foregoing metals; a polymer; ceramics; glass; a composite comprising polymer and fiberglass; quartz; silicon; or a combination of two or more thereof.

15. The process of claim 1 wherein the product exiting the microchannel reactor is at a temperature in the range of about 100 to about 1000° C., and during step (C) it is cooled to a temperature in the range of about 50 to about 300° C. in about 5 to about 100 milliseconds.

16. The process of claim 1 wherein the microchannel reactor has an entrance and an exit, the product exits the microchannel reactor through the exit, and at least part of the product exiting the microchannel reactor is recycled to the entrance to the microchannel reactor.

17. The process of claim 1 wherein the hydrocarbon reactant comprises: a saturated aliphatic compound, an unsaturated aliphatic compound, an aldehyde, an alkyl or alkylene substituted aromatic compound, or a mixture of two or more thereof.

18. The process of claim 1 wherein the hydrocarbon reactant comprises an alkane containing 1 to about 20 carbon atoms per molecule.

19. The process of claim 1 wherein the hydrocarbon reactant comprises methane, ethane, propane, isopropane, butane, isobutane, a pentane, a hexane, a heptane, an octane, a nonane, a decane, or a mixture of two or more thereof.

20. The process of claim 1 wherein the hydrocarbon reactant comprises an alkene containing 2 to about 20 carbon atoms.

21. The process of claim 1 wherein the hydrocarbon reactant comprises ethylene; propylene; 1-butene; 2-butene; isobutylene; 1-pentene; 2-pentene; 3-methyl-1-butene; 2-methyl-2-butene; 1-hexene; 2,3-dimethyl-2-butene; 1-heptene; 1-octene; 1-nonene; 1-decene; or a mixture of two or more thereof.

22. The process of claim 1 wherein the hydrocarbon reactant comprises a polyene containing 3 to about 20 carbon atoms.

23. The process of claim 1 wherein the hydrocarbon reactant comprises 1,2-propadiene; 1,3-butadiene; 2-methyl-1,3-butadiene; 1,3-pentadiene; 1,4-pentadiene; 1,5-hexadiene; 2,4-hexadiene; 2,3-dimethyl-1,3-butadiene; or a mixture of two or more thereof.

24. The process of claim 1 wherein the hydrocarbon reactant comprises an aldehyde containing 1 to about 20 carbon atoms.

25. The process of claim 1 wherein the hydrocarbon reactant comprises formaldehyde; acetaldehyde; propionaldehyde; n-butyraldehyde; n-valeraldehyde; caproaldehyde; acrolein; tran-2-cis-6-nonadienal; n-heptylaldehyde; trans-2-hexenal; hexadeconal; benzaldehyde; phenylacetaldehyde; o-tolualdehyde; m-tolualdehyde; p-tolualdehyde; salicylaldehyde; p-hydroxybenzaldehyde; or a mixture of two or more thereof.

26. The process of claim 1 wherein the hydrocarbon reactant comprises an alkyl or alkylene substituted aromatic compound.

27. The process of claim 1 wherein the hydrocarbon reactant comprises toluene, o-xylene, m-xylene, p-xylene, hemimellitene, pseudocumene, mesitylene, prehnitene, isodurene, durene, pentamethylbenzene, hexamethylbenzene, ethylbenzene, n-propylbenzene, cumene, n-butylbenzene, isobutylbenzene, sec-butylbenzene, tert-butylbenzene, p-cymene, styrene, or a mixture of two or more thereof.

28. The process of claim 1 wherein the reactant composition comprises ammonia.

29. The process of claim 1 wherein the source of oxygen comprises air.

30. The process of claim 1 wherein the reactant composition further comprises a diluent material.

31. The process of claim 11 wherein the process microchannels are cooled using a heat exchange fluid flowing through the heat exchange channels.

32. The process of claim 31 wherein the heat exchange fluid undergoes a phase change as it flows through the heat exchange channels.

33. The process of claim 11 wherein the process microchannels are cooled by an endothermic chemical reaction conducted in the heat exchange channels.

34. The process of claim 33 wherein the endothermic chemical reaction comprises a steam reforming reaction or a dehydrogenation reaction.

35. The process of claim 11 wherein the reactant composition flows through the process microchannels in a first direction, and a heat exchange fluid flows through the heat exchange channels in a second direction, the second direction being cross current relative to the first direction.

36. The process of claim 11 wherein the reactant composition flows through the process microchannels flow in a first direction, and a heat exchange fluid flows through the heat exchange channels in a second direction, the second direction being cocurrent relative to the first direction.

37. The process of claim 11 wherein the hydrocarbon reactant composition flows through the process microchannels in a first direction, and a heat exchange fluid flows through the heat exchange channels in a second direction, the second direction being counter current relative to the first direction.

38. The process of claim 11 wherein a heat exchange fluid flows through the heat exchange channels, the heat exchange fluid comprising air, steam, liquid water, carbon dioxide, gaseous nitrogen, liquid nitrogen, a gaseous hydrocarbon or a liquid hydrocarbon.

39. The process of claim 1 wherein the catalyst comprises a flow-by structure or a flow-through structure.

40. The process of claim 7 wherein the process microchannels have an interior surface and the catalyst is coated on the interior surface of the process microchannels.

41. The process of claim 1 wherein the catalyst is in the form of particulate solids, foam, felt, wad, honeycomb, insertable fin, or a combination of two or more thereof.

42. The process of claim 1 wherein the catalyst has a serpentine configuration.

43. The process of claim 1 wherein the catalyst is in the form of a flow-by structure with an adjacent gap, a foam with an adjacent gap, a fin structure with gaps, a washcoat on an inserted substrate, or a gauze that is parallel to the flow direction with a corresponding gap for flow.

44. The process of claim 1 wherein the catalyst comprises a porous support, an interfacial layer, and a catalytic material.

45. The process of claim 1 wherein the catalyst comprises a porous support, a buffer layer, an interfacial layer, and a catalytic material.

46. The process of claim 1 wherein the catalyst comprises at least one metal, metal oxide or mixed metal oxide of a metal selected from the group consisting of Mo, W, V, Nb, Sb, Sn, Pt, Pd, Cs, Zr, Cr, Mg, Mn, Ni, Co, Ce, and mixtures of two or more thereof.

47. The process of claim 46 wherein the catalyst further comprises a metal, oxide or mixed metal oxide of an alkali or alkaline earth metal, a transition metal, a rare earth metal, a lanthanide, or a mixture of two or more thereof.

48. The process of claim 44 wherein the catalyst further comprises P, Bi or a mixture thereof.

49. The process of claim 1 wherein the catalyst comprises a support comprising a metal oxide, silica, mesoporus material, refractory material, or a combination of two or more thereof.

50. The process of claim 1 wherein the contact time of the reactant composition and/or product with the catalyst is from about 0.1 milliseconds to about 100 seconds.

51. The process of claim 7 wherein the temperature of the reactant composition entering the process microchannels is in the range of about 150° C. to about 1000° C.

52. The process of claim 7 wherein the pressure of the reactant composition entering the process microchannels is in the range of about 0.5 to about 100 atmospheres.

53. The process of claim 7 wherein the space velocity for the flow of the reactant composition and product through the process microchannels is at least about 100 hr.$^{-1}$.

54. The process of claim 1 wherein the product comprises a monool or a polyol.

55. The process of claim 1 wherein the product comprises methanol, ethyl alcohol, propyl alcohol, butyl alcohol, isobutyl alcohol, pentyl alcohol, cyclopentyl alcohol, crotyl alcohol, hexyl alcohol, cyclohexyl alcohol, allyl alcohol, benzyl alcohol, glycerol, or a mixture of two or more thereof.

56. The process of claim 1 wherein the product comprises an epoxide.

57. The process of claim 1 wherein the product comprises ethylene oxide, propylene oxide, butylene oxide, isobutylene oxide, cyclopentene oxide, cyclohexene oxide, styrene oxide, or a mixture of two or more thereof.

58. The process of claim 1 wherein the product comprises an aldehyde.

59. The process of claim 1 wherein the product comprises formaldehyde; acetaldehyde; propionaldehyde; n-butyraldehyde; n-valeraldehyde; caproaldehyde; acrolein; tran-2-cis-6-nonadienal; n-heptylaldehyde; trans-2-hexenal; hexadeconal; benzaldehyde; phenylacetaldehyde; o-tolualdehyde; m-tolualdehyde; p-tolualdehyde; salicylaldehyde; p-hydroxybenzaldehyde; or a mixture of two or more thereof.

60. The process of claim 1 wherein the product comprises a carboxylic acid, a carboxylic acid anhydride, or a mixture thereof.

61. The process of claim 1 wherein the product comprises formic acid, acetic acid, propionic acid, butyric acid, isobutyric acid, valeric acid, caproic acid, caprylic acid, capric acid, acrylic acid, methacrylic acid, benzoic acid, toluic acid, phthalic acid, salicylic acid, acetic anhydride, maleic anhydride, phthalic anhydride, benzoic anhydride, or a mixture of two or more thereof.

62. The process of claim 1 wherein the product comprises an ester.

63. The process of claim 1 wherein the product comprises methylacetate, vinyl acetate, ethyl acetate, n-propyl acetate, n-butyl acetate, n-pentyl acetate, isopentyl acetate, benzyl acetate, phenyl acetate, or a mixture of two or more thereof.

64. The process of claim 1 wherein the product comprises a nitrile.

65. The process of claim 1 wherein the product comprises formonitrile, acrylonitrile, methacrylonitrile, or a mixture of two or more thereof.

66. The process of claim 1 wherein the fluid hydrocarbon reactant comprises methane, and the product comprises methanol, formaldehyde, formontrile, or a mixture of two or more thereof.

67. The process of claim 1 wherein the fluid hydrocarbon reactant comprises ethane, and the product comprises ethyl alcohol, ethylene oxide, acetic acid, vinyl acetate, or a mixture of two or more thereof.

68. The process of claim 1 wherein the fluid hydrocarbon reactant comprises ethylene, and the product comprises ethyl alcohol, ethylene oxide, acetic acid, vinyl acetate, or a mixture of two or more thereof.

69. The process of claim 1 wherein the fluid hydrocarbon reactant comprises propane, and the product comprises propylene oxide, acrylic acid, acrolein, acrylonitrile, or a mixture thereof.

70. The process of claim 1 wherein the fluid hydrocarbon reactant comprises propylene, and the product comprises propylene oxide, acrylic acid, acrolein, acrylonitrile, or a mixture thereof.

71. The process of claim 1 wherein the fluid hydrocarbon reactant comprises n-butane, and the product comprises n-butanol, maleic anhydride, or a mixture thereof.

72. The process of claim 1 wherein the fluid hydrocarbon reactant comprises n-butene, and the product comprises n-butanol, maleic anhydride, or a mixture thereof.

73. The process of claim 1 wherein the fluid hydrocarbon reactant comprises isobutane, and the product comprises isobutanol, methacrylic acid, methacrylonitrile, or a mixture thereof.

74. The process of claim 1 wherein the fluid hydrocarbon reactant comprises isobutylene, and the product comprises isobutanol, methacrylic acid, methacrylonitrile, or a mixture thereof.

75. The process of claim 1 wherein the fluid hydrocarbon reactant comprises toluene, and the product comprises benzyl alcohol, benzoic acid, benzaldehyde, or a mixture thereof.

76. The process of claim 1 wherein the fluid hydrocarbon reactant comprises xylene, and the product comprises toluic acid, phthalic acid, phthalic anhydride, or a mixture thereof.

77. The process of claim 1 wherein the fluid hydrocarbon reactant comprises cyclopentene, and the product comprises cyclopentene oxide.

78. The process of claim 1 wherein the fluid hydrocarbon reactant comprises cyclohexene, and the product comprises cyclohexene oxide.

79. The process of claim 1 wherein the fluid hydrocarbon reactant comprises styrene, and the product comprises styrene oxide.

80. The process of claim 1 wherein the fluid hydrocarbon reactant comprises acrolein and the product comprises acrylic acid.

81. The process of claim 11 wherein a heat exchange fluid flows through the heat exchange channels, the total pressure drop for the heat exchange fluid flowing through the heat exchange channels being up to about 10 atmospheres.

82. A process for converting a hydrocarbon reactant to a product, the process comprising:
  (A) flowing a reactant composition comprising the hydrocarbon reactant, and oxygen or a source of oxygen, and optionally ammonia, in a microchannel reactor in contact with a catalyst to convert the hydrocarbon reactant to the product, the product comprising an oxygenate or a nitrile; the hydrocarbon reactant undergoing an exothermic reaction in the microchannel reactor; the microchannel reactor comprising a plurality of process microchannels containing the catalyst, each of the process microchannels having an entrance, an exit and an elongated section extending between the entrance and the exit, each of the process microchannels further comprising at least one additional entrance in the elongated section, the hydrocarbon reactant and optionally ammonia flowing through the entrance into the process microchannels, the oxygen or source of oxygen entering the process microchannels through the at least one additional entrance and contacting the hydrocarbon reactant and optionally ammonia in the process microchannels;
  (B) transferring heat from the microchannel reactor to a heat exchanger during step (A), the heat exchanger comprising heat exchange channels, the heat exchange channels being adjacent to the process microchannels; and
  (C) quenching the product from step (A).

83. A process for converting a hydrocarbon reactant to a product, the process comprising:
  (A) flowing a reactant composition comprising the hydrocarbon reactant, and oxygen or a source of oxygen in a microchannel reactor in contact with a catalyst to convert the hydrocarbon reactant to the product, the product comprising an oxygenate, the oxygen or source of oxygen being in the form of a gas, the hydrocarbon reactant undergoing an exothermic reaction in the microchannel reactor, the microchannel reactor comprising a plurality of process microchannels containing the catalyst, the hydrocarbon reactant flowing in the process microchannels, the oxygen or source of oxygen entering the process microchannels at different points along the length of the process microchannels;
  (B) transferring heat from the microchannel reactor to a heat exchanger during step (A), the heat exchanger comprising heat exchange microchannels in thermal contact with the process microchannels; and
  (C) quenching the product from step (A).

84. A process for converting a hydrocarbon reactant to a product, the process comprising:
  (A) flowing a reactant composition comprising the hydrocarbon reactant, and oxygen or a source of oxygen, and ammonia, in a microchannel reactor in contact with a catalyst to convert the hydrocarbon reactant to the product, the product comprising a nitrile, the oxygen or source of oxygen being in the form of a gas, the hydrocarbon reactant undergoing an exothermic reaction in the microchannel reactor, the microchannel reactor comprising a plurality of process microchannels containing the catalyst, the hydrocarbon reactant and ammonia flowing in the process microchannels, the oxygen or source of oxygen being added to the hydrocarbon reactant and ammonia at different points along the length of the process microchannels;
  (B) transferring heat from the microchannel reactor to a heat exchanger during step (A), the heat exchanger comprising heat exchange microchannels in thermal contact with the process microchannels; and
  (C) quenching the product from step (A).

85. A process for converting a hydrocarbon reactant to a product, the process comprising:
  (A) flowing a reactant composition comprising the hydrocarbon reactant, and oxygen or a source of oxygen, and optionally ammonia, in a microchannel reactor in contact with a catalyst to convert the hydrocarbon reactant to the product, the product comprising an oxygenate or a nitrile, the microchannel reactor comprising at least one process microchannel, the catalyst being in the process microchannel, the oxygen or source of oxygen being mixed with the hydrocarbon reactant and optionally ammonia in the process microchannel, the hydrocarbon reactant undergoing an exothermic reaction in the process microchannel;

(B) transferring heat from the process microchannel to a heat exchanger during (A); and (C) quenching the product formed in (A) by reducing the temperature of the product by up to about 950° C. within a period of up to about 500 milliseconds.

86. A process for converting a hydrocarbon reactant to a product, the process comprising:

(A) flowing a reactant composition comprising the hydrocarbon reactant, and oxygen or a source of oxygen, and optionally ammonia, in a microchannel reactor in contact with a catalyst to convert the hydrocarbon reactant to the product, the product comprising an oxygenate or a nitrile, the microchannel reactor comprising at least one process microchannel, the catalyst being in the process microchannel, the oxygen or source of oxygen being mixed with the hydrocarbon reactant and optionally ammonia in the process microchannel, the hydrocarbon reactant undergoing an exothermic reaction in the process microchannel;

(B) transferring heat from the process microchannel to a heat exchanger during (A); and (C) quenching the product formed in (A) by flowing the product through a quenching apparatus having a dimension equal to or below the quench diameter of the reaction.

87. A process for converting a hydrocarbon reactant to a product, the process comprising:

(A) flowing a reactant composition comprising the hydrocarbon reactant, and oxygen or a source of oxygen, and optionally ammonia, in a microchannel reactor in contact with a catalyst to convert the hydrocarbon reactant to the product, the product comprising an oxygenate or a nitrile, the microchannel reactor comprising at least one process microchannel, the catalyst being in the process microchannel, the hydrocarbon reactant undergoing an exothermic reaction in the process microchannel; and (B) transferring heat from the process microchannel to a heat exchanger during (A), the heat exchanger comprising at least one heat exchange channel in thermal contact with the process microchannel, a heat exchange fluid in the heat exchange channel undergoing phase change in the heat exchange channel.

88. A process for converting a hydrocarbon reactant to a product, the process comprising:

(A) flowing a reactant composition comprising the hydrocarbon reactant, and oxygen or a source of oxygen, and optionally ammonia, in a microchannel reactor in contact with a catalyst to convert the hydrocarbon reactant to the product, the product comprising an oxygenate or a nitrile, the microchannel reactor comprising at least one process microchannel, the catalyst being in the process microchannel, the hydrocarbon reactant undergoing an exothermic reaction in the process microchannel; and (B) transferring heat from the process microchannel to a heat exchanger during (A), the heat exchanger comprising at least one heat exchange channel in thermal contact with the process microchannel, an endothermic reaction being conducted in the heat exchange channel.

89. A process for converting a hydrocarbon reactant to a product, the process comprising:

(A) flowing a reactant composition comprising the hydrocarbon reactant, and oxygen or a source of oxygen, and optionally ammonia, in a microchannel reactor in contact with a catalyst to convert the hydrocarbon reactant to the product, the product comprising an oxygenate or a nitrile, the microchannel reactor comprising at least one process microchannel, the catalyst being in the process microchannel, the hydrocarbon reactant undergoing an exothermic reaction in the process microchannel;

(B) transferring heat from the process microchannel to a heat exchanger during (A) to maintain the temperature of the reactant composition at the entrance to the process microchannel within about 200° C. of the temperature of the product exiting the process microchannel, the heat exchanger comprising a heat exchange fluid which undergoes a phase change or an endothermic reaction.

90. A process for converting a hydrocarbon reactant to a product, the process comprising:

(A) flowing a reactant composition comprising the hydrocarbon reactant, and oxygen or a source of oxygen, and optionally ammonia, in a microchannel reactor in contact with a catalyst to convert the hydrocarbon reactant to the product, the product comprising an oxygenate or a nitrile, the microchannel reactor comprising at least one process microchannel, the catalyst being in the process microchannel, the oxygen or source of oxygen flowing into the process microchannel to contact the hydrocarbon reactant and optionally ammonia at various points along the length of the process microchannel, the hydrocarbon reactant undergoing an exothermic reaction in the process microchannel; and (B) transferring heat from the process microchannel to a heat exchanger during (A).

91. A process for converting a hydrocarbon reactant to a product, the process comprising:

(A) flowing a reactant composition comprising the hydrocarbon reactant, and oxygen or a source of oxygen, and optionally ammonia, in a microchannel reactor in contact with a catalyst to convert the hydrocarbon reactant to the product, the product comprising an oxygenate or a nitrile, the microchannel reactor comprising at least one process microchannel, the catalyst being in the process microchannel, the oxygen or source of oxygen being mixed with the hydrocarbon reactant and optionally ammonia in the process microchannel, the hydrocarbon reactant undergoing an exothermic reaction in the process microchannel; and (B) transferring heat from the process microchannel to a heat exchanger during (A).

* * * * *